US010765988B2

(12) United States Patent
Wells et al.

(10) Patent No.: US 10,765,988 B2
(45) Date of Patent: Sep. 8, 2020

(54) APPARATUS AND METHOD FOR TREATING GAS IN A LIQUID MEDIUM WITH ULTRASONIC ENERGY FOR CHEMICAL REACTION

(71) Applicant: Coldharbour Marine Limited, Linby (GB)

(72) Inventors: Mark Wells, South Normanton (GB); Andrew Marshall, South Normanton (GB); Peter James Dobson, Oxford (GB)

(73) Assignee: Coldharbour Marine Limited, Linby (GB)

(*) Notice: Subject to any disclaimer, the term of this patent is extended or adjusted under 35 U.S.C. 154(b) by 553 days.

(21) Appl. No.: 15/029,099

(22) PCT Filed: Oct. 14, 2014

(86) PCT No.: PCT/GB2014/053089
§ 371 (c)(1),
(2) Date: Apr. 13, 2016

(87) PCT Pub. No.: WO2015/056003
PCT Pub. Date: Apr. 23, 2015

(65) Prior Publication Data
US 2016/0243488 A1    Aug. 25, 2016

(30) Foreign Application Priority Data

Oct. 14, 2013   (GB) .................................... 1318187.0
Sep. 18, 2014   (GB) .................................... 1416538.5

(51) Int. Cl.
*B01D 53/00*    (2006.01)
*B01J 19/10*    (2006.01)
(Continued)

(52) U.S. Cl.
CPC ....... *B01D 53/007* (2013.01); *B01D 53/8671* (2013.01); *B01D 53/94* (2013.01);
(Continued)

(58) Field of Classification Search
CPC .. B01D 53/007; B01D 53/94; B01D 53/8671; B01D 2258/0283; B01D 2259/816;
(Continued)

(56) References Cited

U.S. PATENT DOCUMENTS

| 347,196 A | 8/1886 | Pohle |
|---|---|---|
| 1,054,629 A | 2/1913 | Warwick |

(Continued)

FOREIGN PATENT DOCUMENTS

| CH | 637034 | 7/1983 |
|---|---|---|
| CN | 87100504 A | 8/1987 |

(Continued)

OTHER PUBLICATIONS

International Search Report, International Application No. PCT/GB2014/053089, dated Apr. 22, 2015, 9 pages.
(Continued)

*Primary Examiner* — Nicholas A Smith
*Assistant Examiner* — Colleen M Raphael
(74) *Attorney, Agent, or Firm* — Myers Bigel, P.A.

(57) ABSTRACT

A gas conversion apparatus (100) for converting a process gas to one or more other gases comprises: means (105) for introducing process gas into a liquid medium in a column (125); and an ultrasonic energy generator (140) arranged to generate ultrasonic energy, the apparatus (100) being configured to launch ultrasonic energy generated by the generator (140) into the liquid medium such that process gas is exposed to ultrasonic energy, the apparatus (100) being arranged to allow collection of process gas that has been exposed to ultrasonic energy. The apparatus (100) also
(Continued)

preferably comprises a microbubble generator (120) to generate microbubbles of the process gas for exposure to the ultrasonic energy. The ultrasonic energy generator (140) may be configured to generate ultrasonic energy as a consequence of a flow of a drive gas therethrough.

20 Claims, 11 Drawing Sheets

(51) Int. Cl.

| | | |
|---|---|---|
| F04F 1/18 | (2006.01) | |
| F01N 13/00 | (2010.01) | |
| B01D 53/86 | (2006.01) | |
| B01D 53/94 | (2006.01) | |
| B01J 8/16 | (2006.01) | |
| C07C 1/12 | (2006.01) | |
| F01N 3/04 | (2006.01) | |
| F01N 3/10 | (2006.01) | |
| B63B 13/00 | (2006.01) | |

(52) U.S. Cl.
CPC ............... *B01J 8/16* (2013.01); *B01J 19/10* (2013.01); *C07C 1/12* (2013.01); *F01N 3/043* (2013.01); *F01N 3/103* (2013.01); *F01N 13/009* (2014.06); *F04F 1/18* (2013.01); *B01D 2251/00* (2013.01); *B01D 2255/20738* (2013.01); *B01D 2258/0283* (2013.01); *B01D 2259/816* (2013.01); *B01J 2208/00946* (2013.01); *B01J 2219/0884* (2013.01); *B01J 2219/0892* (2013.01); *B63B 13/00* (2013.01); *C07C 2523/745* (2013.01); *F01N 2250/08* (2013.01)

(58) Field of Classification Search
CPC ...... B01D 2251/00; B01D 2255/20738; F01N 3/043; F01N 3/103; F01N 13/009; F01N 2250/08; C07C 1/12; C07C 2523/745; B01J 8/16; B01J 19/10; B01J 2208/00946; B01J 2219/0884; B01J 2219/0892; F04F 1/18; B63B 13/00
USPC .................. 204/157.42, 157.62; 422/20
See application file for complete search history.

(56) References Cited

U.S. PATENT DOCUMENTS

| | | | |
|---|---|---|---|
| 1,604,419 A | 6/1923 | Oliphant | |
| 1,698,619 A | 1/1929 | Blow | |
| 1,712,695 A | 5/1929 | Engstrand | |
| 2,265,762 A * | 12/1941 | McKittrick | B01D 53/1475 423/228 |
| 2,632,513 A | 3/1953 | Bennett | |
| 2,800,444 A * | 7/1957 | Hughes | B01J 19/10 204/157.15 |
| 3,172,370 A | 3/1965 | Hoff | |
| 3,230,923 A | 1/1966 | Hughes | |
| 3,393,519 A | 7/1968 | Mitchell | |
| 3,427,989 A | 2/1969 | Bostock et al. | |
| 3,433,174 A | 3/1969 | Chenoweth | |
| 3,694,106 A | 9/1972 | Walker | |
| 3,834,364 A * | 9/1974 | Bartholomew | F02M 27/08 123/531 |
| 4,408,719 A | 10/1983 | Last | |
| 5,326,468 A | 7/1994 | Cox | |
| 5,735,600 A | 4/1998 | Wyness et al. | |
| 6,221,260 B1 | 4/2001 | Chahine | |
| 6,402,965 B1 | 6/2002 | Sullivan et al. | |
| 6,540,922 B1 | 4/2003 | Cordemans et al. | |
| 6,770,248 B2 | 8/2004 | Haggett | |
| 6,821,442 B1 | 11/2004 | Watten | |

| | | | |
|---|---|---|---|
| 2002/0174814 A1 | 11/2002 | Hunter | |
| 2003/0132165 A1 | 7/2003 | De Meulenaer et al. | |
| 2005/0006313 A1 | 1/2005 | Swinnen et al. | |
| 2006/0118495 A1 | 6/2006 | Kondratalv | |
| 2008/0128362 A1 | 6/2008 | Babaev | |
| 2008/0236160 A1 * | 10/2008 | Glotov | B01F 5/162 60/530 |
| 2008/0250715 A1 | 10/2008 | Cooper et al. | |
| 2009/0023821 A1 | 1/2009 | Quapp et al. | |
| 2009/0145595 A1 | 6/2009 | Mazzanti | |
| 2010/0224571 A1 | 9/2010 | Babaev et al. | |
| 2011/0306931 A1 | 12/2011 | Kamen | |
| 2012/0329657 A1 | 12/2012 | Eastman et al. | |
| 2013/0089480 A1 | 4/2013 | Dickinson et al. | |
| 2013/0160688 A1 * | 6/2013 | Whiteside | B08B 9/0326 210/748.03 |
| 2013/0177922 A1 * | 7/2013 | Laugharn, Jr. | B01F 11/0283 422/128 |
| 2014/0121346 A1 * | 5/2014 | Tang | B01D 53/1425 96/144 |
| 2015/0315047 A1 * | 11/2015 | Whiteside | F04F 1/18 210/748.03 |

FOREIGN PATENT DOCUMENTS

| | | |
|---|---|---|
| CN | 101138700 | 3/2008 |
| CN | 101792692 A | 8/2010 |
| CN | 101618306 | 5/2012 |
| CN | 102302919 | 8/2013 |
| CN | 103240046 | 8/2013 |
| DE | 40 37 899 A1 | 6/1992 |
| DE | 195 24 712 | 1/1997 |
| DE | 197 00 202 A1 | 7/1998 |
| DE | 10 2004 042984 A1 | 3/2006 |
| EP | 0 232 000 A1 | 8/1987 |
| EP | 0 442 454 A1 | 8/1991 |
| EP | 0770424 | 5/1997 |
| EP | 0 963 784 A1 | 12/1999 |
| FR | 2 809 179 A1 | 11/2001 |
| GB | 150698 | 8/1919 |
| GB | 624385 A | 6/1949 |
| GB | 1063388 | 8/1964 |
| GB | 1063860 A | 3/1967 |
| GB | 1 074 099 | 6/1967 |
| GB | 1241377 | 5/1969 |
| GB | 2 432 799 A | 6/2007 |
| GB | 2470070 A | 10/2010 |
| JP | S50125718 A | 10/1975 |
| JP | S5489366 A | 7/1979 |
| JP | 56114897 | 9/1981 |
| JP | S60227887 | 11/1985 |
| JP | S6245398 A | 2/1987 |
| JP | 1310200 A | 12/1989 |
| JP | 2090982 A | 3/1990 |
| JP | H04026100 U | 3/1992 |
| JP | H06134347 A | 5/1994 |
| JP | H06277690 A | 10/1994 |
| JP | 2000000447 A | 1/2000 |
| JP | 2000205200 A | 7/2000 |
| JP | 2000240600 A | 9/2000 |
| JP | 2000516522 A | 12/2000 |
| JP | 2003049800 A | 2/2003 |
| JP | 2004237144 A | 8/2004 |
| JP | 2005291171 A | 10/2005 |
| JP | 2006043674 A | 2/2006 |
| JP | 2006136819 | 6/2006 |
| JP | 2007113295 A | 5/2007 |
| JP | 2007515289 A | 6/2007 |
| JP | 2007229577 A | 9/2007 |
| JP | 2008520473 A | 6/2008 |
| JP | 2009022941 A | 2/2009 |
| JP | 2009056442 A | 3/2009 |
| JP | 2009513333 A | 4/2009 |
| JP | 2009-126794 A | 6/2009 |
| JP | 2009131827 | 6/2009 |
| JP | 2010000490 A | 1/2010 |
| JP | 2010-36148 A | 2/2010 |
| JP | 2010036148 A | 2/2010 |

(56) References Cited

FOREIGN PATENT DOCUMENTS

| | | |
|---|---|---|
| JP | 2011072982 A | 4/2011 |
| RU | 2248469 C1 | 3/2005 |
| SU | 500379 A1 | 1/1976 |
| WO | WO 98/01394 | 1/1998 |
| WO | WO 2005/005322 A | 1/2005 |
| WO | WO 2005/061394 A1 | 7/2005 |
| WO | WO 2006/080969 A1 | 8/2006 |
| WO | WO 2007/049139 A1 | 5/2007 |
| WO | WO 2007/122731 A1 | 11/2007 |
| WO | WO 2008/029311 | 3/2008 |
| WO | WO 2010/128336 A1 | 11/2010 |
| WO | WO 2012/001415 | 1/2012 |
| WO | WO 2013/093527 | 6/2013 |
| WO | WO 2013/108550 A1 | 7/2013 |

OTHER PUBLICATIONS

Written Opinion of the International Searching Authority, International Application No. PCT/GB2014/053089, dated Apr. 22, 2015, 11 pages.
Combined Search and Examination Report, GB 1418204.2, dated Apr. 15, 2015, 8 pages.
Patents Act 1977: Examination Report under Section 18(3), UK IPO Application No. GB1411447.4, dated Aug. 2, 2017, 5 pp.
"What is amplitude?", downloaded Jul. 21, 2017 from http://www.indiana.edu/~emusic/acoustic/amplitude.htm, 6 pp.
Korean Intellectual Property Office Notice of Submission of Opinion corresponding to Korean Patent Application No. 10-2013-7002408, dated Dec. 14, 2017 (21 pages).

\* cited by examiner

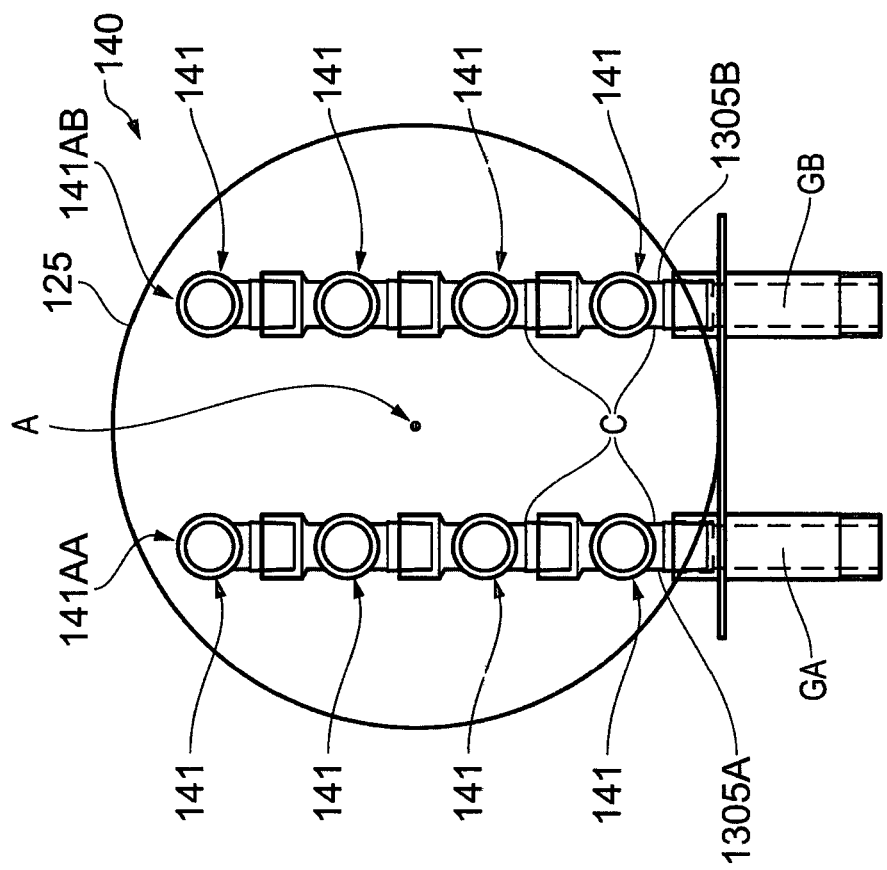
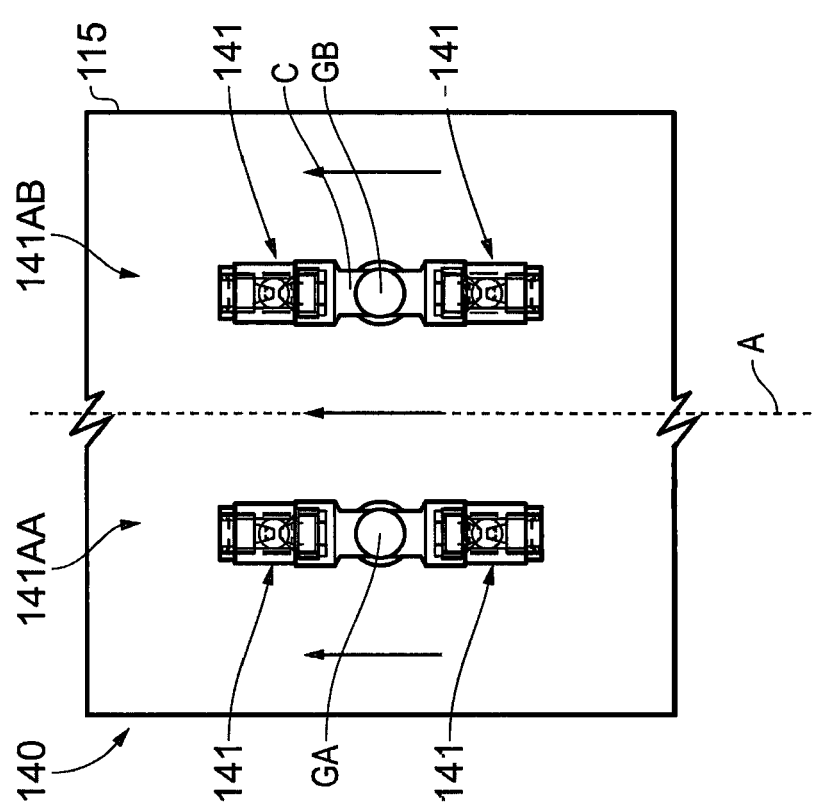
FIG. 3(b)
FIG. 3(a)

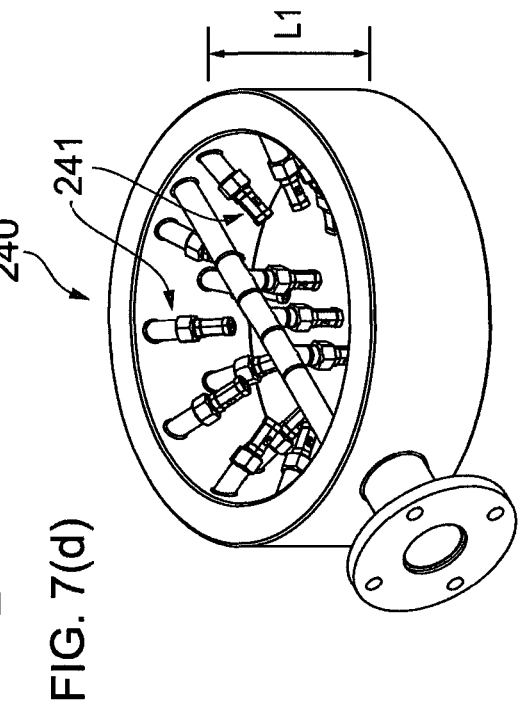
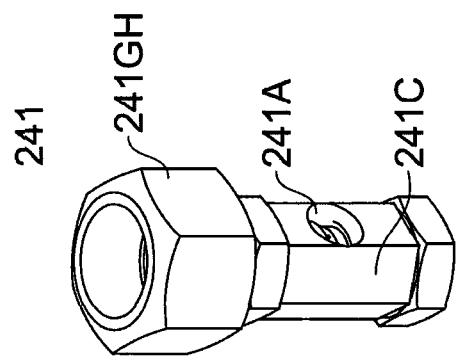
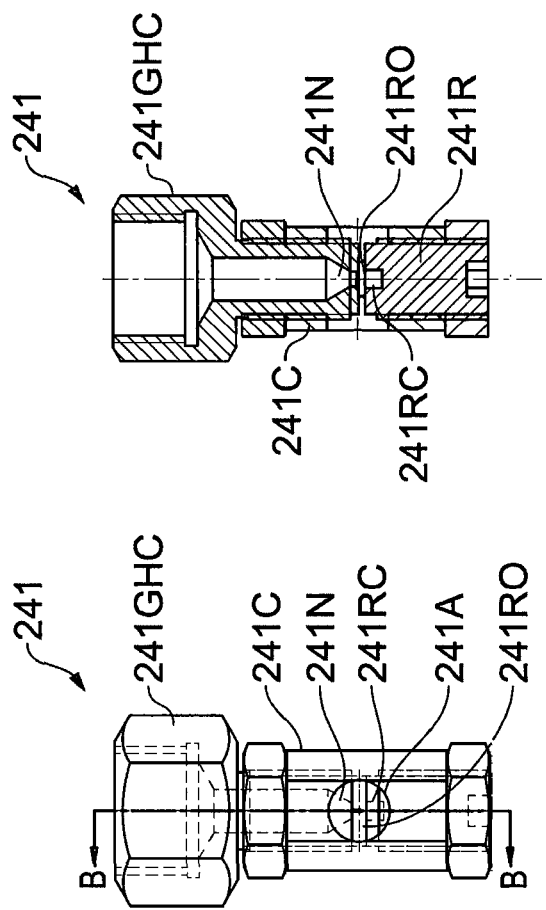

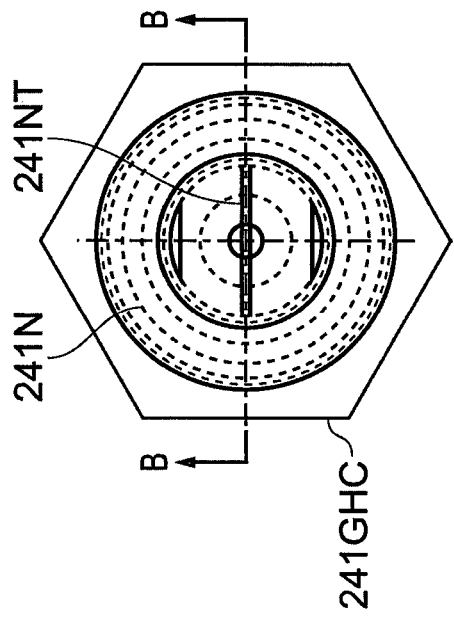
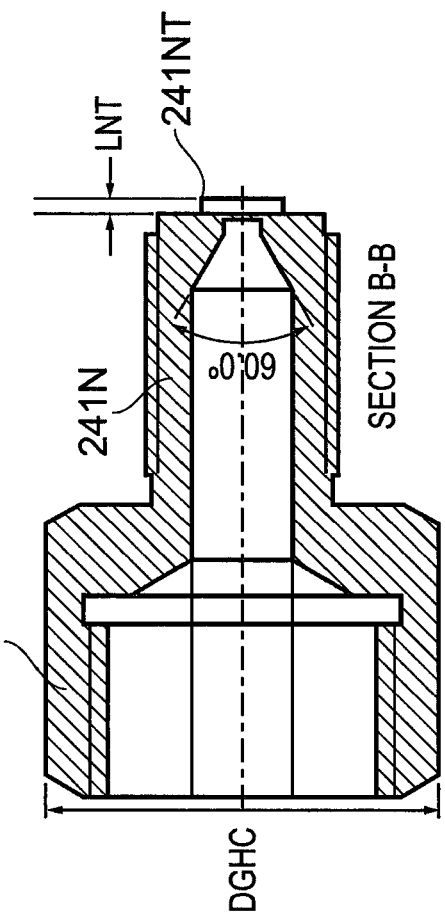
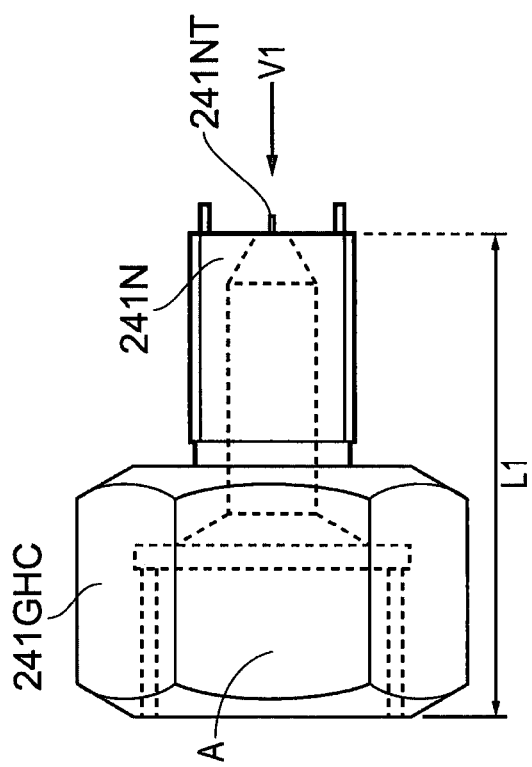
FIG. 8(b)
FIG. 8(c)
FIG. 8(a)

APPARATUS AND METHOD FOR TREATING GAS IN A LIQUID MEDIUM WITH ULTRASONIC ENERGY FOR CHEMICAL REACTION

RELATED APPLICATIONS

This application is a 35 U.S.C. § 371 national stage application of PCT Application No. PCT/GB2014/053089, filed on Oct. 14, 2014, which claims priority from Great Britain Patent Application Nos. 1318187.0 and 1416538.5, filed Oct. 14, 2013 and Sep. 18, 2014, respectively, the contents of which are incorporated herein by reference in their entireties. The above-referenced PCT International Application was published in the English language as International Publication No. WO 2015/056003 A2 on Apr. 23, 2015.

INCORPORATION BY REFERENCE

The content of WO2013/093527 is hereby incorporated by reference. The content of Wang et al, J. Phys. Chem. Lett. 2010, 1, 48-53, is hereby incorporated herein by reference.

TECHNICAL FIELD

The present invention relates to the handling and treatment of greenhouse gases. In particular but not exclusively the invention relates to handling and treatment of greenhouse gases such as combustion gases emitted from an industrial source such as a coal, oil or gas-fired power station or from one or more other sources such as internal combustion engines. In certain aspects the invention also relates to treatment of liquids in storage vessels.

BACKGROUND

It is understood that emissions of combustion gases from industrial plants such as coal, oil or gas-fired power stations and other sources including internal combustion engines are harmful to the environment. Emissions of carbon dioxide are of particular concern and there is substantial interest in reducing the amount of carbon dioxide emitted into the atmosphere.

One method of reducing emissions is to capture the carbon dioxide and store it until an economical treatment method is available for converting carbon dioxide to a less harmful or even beneficial form, such as to carbon and oxygen ($O_2$). However, storage of carbon dioxide is costly and merely postpones the problem of conversion of the gas.

It is an aim of the present invention to address disadvantages associated with the prior art.

SUMMARY OF THE INVENTION

Embodiments of the invention may be understood with reference to the appended claims.

Aspects of the present invention provide an apparatus and a method.

In an aspect of the invention for which protection is sought there is provided gas conversion apparatus for converting one or more reactant chemical species comprised by a process gas to one or more product chemical species, comprising:

means for introducing process gas into a carrier liquid medium; and an ultrasonic energy generator arranged to generate ultrasonic energy, the apparatus being configured to launch ultrasonic energy generated by the generator into the liquid medium such that process gas is exposed to ultrasonic energy, the apparatus being arranged to allow collection of one or more product chemical species.

Embodiments of the present invention have the feature that process gas may be subject to ultrasonic energy resulting in the conversion of the process gas or one or more chemical species thereof to one or more other chemical species such as one or more other gases.

By launching the ultrasonic energy into a liquid medium into which process gas has been introduced, the process gas may be subjected to cavitation in collapsing bubbles, resulting in the conversion of the process gas from one chemical species, such as carbon dioxide, to one or more other chemical species, such as one or more hydrocarbons and/or optionally one or more further species. For example, in some embodiments the process gas may be or may comprise carbon dioxide as reactant chemical species, carbon dioxide being converted to product chemical species methane and oxygen. Other conversion reactions may also be useful. For example in some embodiments carbon dioxide may be converted to a different hydrocarbon in addition or instead, such as ethane, propane, or any other suitable hydrocarbon or hydrocarbons. In some embodiments carbon dioxide may be converted to a non-hydrocarbon material. In some embodiments, one or more compounds other than carbon dioxide may be converted to one or more other forms, whether elemental form, compound form or any other form.

Furthermore, some embodiments of the present invention offer the opportunity to employ alternative energy sources such as renewable energy sources in the production of chemical compounds for use in industry, for example compounds for use as feedstock materials or as sources of chemical energy when reacted, for example when oxidised, optionally by burning in an oxygen-bearing atmosphere. Thus some embodiments of the present invention may be useful in providing means for storing energy generated by renewable energy sources such as solar, wind, wave and/or tidal energy. This renewable energy may be used for example to power a compressor for driving the ultrasonic energy generator, and/or to power a separator for separating chemical species following exposure of process gas to ultrasonic energy.

In some embodiments the process gas may comprise carbon dioxide that is converted to one or more hydrocarbons by exposure to the ultrasonic energy. The hydrocarbon(s) may subsequently be used as a feedstock material, or burned as a fuel when required. In some embodiments the one or more hydrocarbons may be converted to one or more further compounds such as one or more higher alkanes, one or more alkenes, alcohols, or any other suitable compound.

In some embodiments one or more catalyst materials may be used to promote conversion of one or more reactant chemical species to one or more product chemical species, such as copper, zinc oxide, aluminium oxide (alumina, $Al_2O_3$). In some embodiments one or more of these catalysts may be employed to promote synthesis of methanol. In some embodiments, carbon dioxide process gas may be converted to short chain olefins such as ethylene and propylene, either directly or via one or more intermediate compounds such as methanol.

It is to be understood that alkane hydrocarbons of short (1-4) C-chain lengths (methane, ethane, propane, butane) are gaseous at room temperature and pressure, and alkanes only become liquid at such temperatures and pressures at or above to C-5 (pentane). At or above C-16 they are typically solid under these conditions. Some embodiments of the present invention may generate C-n alkanes where n is greater than 1, optionally by use of a suitable catalyst. If one or more hydrocarbons in the form of liquids or solids are produced, a suitable means for separation of the hydrocarbon from the liquid medium or other gaseous or solid medium may be employed.

Advantageously, the ultrasonic generator may be configured to generate ultrasonic energy in response to a flow of a drive gas therethrough.

This has the advantage that process gas may be subject to ultrasonic energy in a highly efficient manner. It is to be understood that relatively high intensity ultrasonic energy may be generated by means of flow of drive gas through a suitable generator, which may for example comprise a whistle device. The amount of energy required to be input to the generator in order to generate the relatively high intensity ultrasonic energy may be less than that which would be required if other ultrasonic energy generation technologies were employed such as electrical generation technologies such as ultrasonic generation technologies based on piezoelectric device technologies.

The apparatus may be configured to cause a flow of process gas in carrier liquid medium through a conduit, and to expose the process gas to ultrasonic energy in the conduit. The conduit may be of any required orientation in some embodiments, such as substantially horizontal. The apparatus may be configured wherein the process gas is exposed to ultrasonic radiation as it travels in a substantially horizontal direction through the conduit. In the case of a conduit mounted in a substantially vertical direction, the process gas may be caused to travel upwardly or downwardly as required. In some embodiments a conduit having an orientation that is neither horizontal nor vertical may be employed. Other arrangements may be useful in some embodiments.

Advantageously, the ultrasonic energy generator may comprise a whistle device, the whistle device being arranged to generate the ultrasonic energy when drive gas is driven through the device.

The apparatus may be arranged to feed the drive gas into the liquid medium after driving the gas through the ultrasonic energy generator.

The apparatus may be arranged wherein the process gas provides or constitutes the drive gas.

That is, the process gas may be caused to pass through the ultrasonic energy generator to generate ultrasonic energy, thereby providing or constituting the drive gas, subsequently passing into the liquid medium where the gas is subjected to ultrasonic energy generated by the ultrasonic energy generator.

In some alternative embodiments, the drive gas and process gas may be different or may be from different sources. For example, in some embodiments the drive gas may be supplied in a closed loop arrangement whereby drive gas that has been forced through the whistle device may be recompressed and forced through the whistle device again, in a substantially continuous loop.

The drive gas may be any suitable gas such as air, nitrogen, carbon dioxide, argon or any other suitable gas or mixture of gases.

The apparatus may comprise a microbubble generator, the apparatus being configured to cause microbubbles of process gas to be generated in the liquid medium and to be subject to irradiation by ultrasonic energy generated by the ultrasonic energy generator.

This feature has the advantage that cavitation of microbubbles of the process gas may be caused. It has been found that if the process gas is in the form of microbubbles containing carbon dioxide, the carbon dioxide may be converted to a hydrocarbon and oxygen as a consequence of irradiation by ultrasonic energy in a highly effective manner.

The apparatus may be operable to pass gas that has been exposed to ultrasonic energy through a separator such as a gas separator to separate gas molecules according to chemical species. The separator may be any suitable separator such as a hollow fibre membrane separator.

It is to be understood that process gas that has been exposed to ultrasonic energy in the manner described above may no longer be of the same chemical species or composition as the process gas prior to exposure to ultrasonic energy. However it is to be understood that gas introduced as process gas and one or more product chemical species may subsequently be passed through a gas separator to separate gas molecules according to chemical species. In some embodiments, gas that has been exposed to ultrasonic energy generated by the ultrasonic energy generator is introduced to a separator for separation of product chemical species therefrom. In some embodiments, gas and liquid that has been exposed to ultrasonic energy is introduced to a separator. The separator may be configured to separate liquid chemical species such as one or more hydrocarbon species from other liquid, optionally in addition to separate gas from liquid. Thus, if in some embodiments the product chemical species include a gas such as molecular oxygen and a liquid, such as a liquid hydrocarbon, for example ethanol or any other liquid hydrocarbon, the separator may separate the molecular oxygen and the product liquid from the liquid medium of the apparatus, which may for example comprise water.

The apparatus may be configured to separate hydrocarbon gases from one or more other gases.

The apparatus may be operable to separate product chemical species such as hydrocarbon chemical species such as hydrocarbon gases from chemical species of the process gas. Thus the apparatus may separate product chemical species such as hydrocarbon gases from one or more chemical species comprised by the process gas prior to irradiation with ultrasonic energy, such as one or more reactant chemical species, which have not reacted to form product chemical species.

The apparatus may be operable to return separated chemical species found in the process gas to the liquid medium for further exposure to ultrasonic energy. Thus, one or more chemical species comprised by the process gas prior to irradiation with ultrasonic energy, such as carbon dioxide, may be subject again to irradiation with ultrasonic energy.

The apparatus may further comprise:
  a gas lift column through which liquid medium may be pumped by gas lift; and
  means for introducing process gas into the column to cause pumping of liquid medium in the column by gas lift,
  the apparatus being configured to launch ultrasonic energy generated by the ultrasonic energy generator into liquid medium in the column such that process gas passing through the column is exposed to ultrasonic energy generated by the generator.

The apparatus may comprise:
a gas lift column; and
means for causing pumping of liquid medium in the column by gas lift,
the apparatus being configured to launch ultrasonic energy generated by the ultrasonic energy generator into liquid medium in the column such that the liquid medium and any solid, liquid and/or gas such as process gas in the liquid medium is exposed to ultrasonic energy generated by the generator.

Optionally, the means for causing pumping of liquid medium in the column by gas lift comprises means for introducing gas into the column. The means for introducing gas into the column to cause pumping of liquid medium by gas lift may comprise means for introducing process gas.

The apparatus may be configured to cause process gas, introduced into the column to cause pumping, to be exposed to ultrasonic energy generated by the generator.

In some embodiments in which the ultrasonic energy generator is powered by a drive gas. The generator may comprise one or more whistle devices in some embodiments. The drive gas may be of substantially the same chemical composition as the process gas. The drive gas may provide the process gas for the apparatus. Thus in some embodiments at least a portion of the process gas that drives the ultrasonic energy generator may be introduced into the column. This may provide at least in part the means for causing pumping of liquid medium in the column by gas lift. Optionally, introduction of process gas into the column may provide substantially all of the gas lift that provides pumping of liquid through the column. In some embodiments process gas may be introduced into the column for exposure to ultrasonic energy The column may be immersed in the liquid medium, optionally in a tank in which the liquid medium is contained. Alternatively the column may be provided externally of the tank.

The present applicant has found that the column of a gas lift pump device provides a beneficial environment in which to subject process gas to ultrasonic energy. This is at least in part because at least some of the process gas introduced into the liquid medium in the column may be confined to the column during exposure to ultrasonic energy. The process gas may thereby be exposed to ultrasonic energy in a more controlled manner than if the gas is introduced into a tank unconstrained. It is to be understood that an intensity of ultrasonic energy to which process gas is subject may depend at least in part on a distance between the source of ultrasonic energy provided by the generator and the process gas as it passes through or past the generator, for example the distance between the source of ultrasonic energy provided by the generator and a bubble of process gas in the liquid medium. The greater the distance, the lower the intensity of the ultrasonic energy in some embodiments. Accordingly it is in general advantageous to expose the process gas to ultrasonic energy as close to the source of ultrasonic energy as possible. The presence of a conduit through which process gas passes and in which the process gas is exposed to ultrasonic energy assists in promoting exposure of process gas to ultrasonic energy close to the source.

The apparatus may be configured to feed drive gas into liquid medium in the column of the gas lift device such that the drive gas is exposed to ultrasonic energy in the column.

In addition or instead, the apparatus may be configured to cause microbubbles generated by the microbubble generator to be subject to irradiation by ultrasonic energy generated by the ultrasonic energy generator.

The apparatus may be arranged wherein the process gas comprises carbon dioxide.

The apparatus may be arranged wherein the process gas comprises at least about 50% carbon dioxide by volume.

The apparatus may be arranged wherein the process gas consists essentially of carbon dioxide.

The apparatus may be configured to separate hydrocarbon gas from gas that has passed through the column. In some embodiments the apparatus may be configured to separate methane from gas that has passed through the column.

In another aspect of the invention for which protection is sought there is provided apparatus according to the previous aspect of the present invention or any embodiment thereof installed in a liquid tank, optionally a liquid holding tank.

Optionally, the tank contains liquid.

Optionally, the liquid is provided with particles of a catalyst material suspended, dissolved or otherwise dispersed therein.

The catalyst particles may comprise iron, optionally iron oxide, optionally a hematite-bearing compound, optionally wherein the catalyst particles consist substantially of hematite.

In one aspect of the invention for which protection is sought there is provided apparatus according to a previous aspect of the invention or any embodiment thereof installed in-line in a processing facility, optionally a liquid processing facility, optionally a waste liquid processing facility. The apparatus may be configured to treat liquid such as waste liquid with a process gas and ultrasonic energy, optionally to treat wastewater, optionally sewage. The apparatus may be configured to destroy one or more biological species such as organisms such as bacteria or virus organisms or other biological species in order to kill the one or more biological species. In some embodiments the apparatus may be configured to convert one or more chemical species in the liquid to one or more other chemical species.

In a further aspect of the invention for which protection is sought there is provided a method of converting a process gas to one or more other gases, comprising:
introducing process gas into a liquid medium; and
generating ultrasonic energy by means of an ultrasonic energy generator, the method comprising launching ultrasonic energy generated by the generator into the liquid medium such that process gas is exposed to ultrasonic energy.

The ultrasonic energy may be generated in response to a flow of a drive gas through the generator.

This feature has the advantage that ultrasonic energy may be generated in a relatively energy efficient manner compared with means of generating ultrasonic energy electrically, such as by means of a piezo-electric generator.

The method may further comprise collecting process gas that has been exposed to ultrasonic energy.

The method may comprise generating ultrasonic energy by means of a whistle device of the generator by driving drive gas through the device.

The method may comprise feeding drive gas into the liquid medium after passing the gas through the whistle device.

Optionally, the process gas provides or constitutes the drive gas.

The method may comprise causing microbubbles to be generated in the liquid medium and to be subjected to irradiation by ultrasonic energy generated by the ultrasonic energy generator.

This feature has the advantage that cavitation of microbubbles of the process gas may be caused. It has been found that if the process gas comprises carbon dioxide, the carbon dioxide may be converted to a hydrocarbon and oxygen in the process of irradiation by ultrasonic energy.

The method may comprise causing gas that has been subjected to ultrasonic energy to be separated according to chemical species by means of a gas separator.

Optionally, causing gas to be separated comprises separating hydrocarbon gases from one or more other gases.

Optionally, causing gas to be separated comprises separating hydrocarbon gases from one or more gases comprised by process gas. For example, causing gas to be separated may comprise separating hydrocarbon gases from gases that are not hydrocarbon gases. The non-hydrocarbon gases may include one or more further reaction products from the conversion of at least some process gas such as one or more chemical compounds or species comprised by the process gas, to hydrocarbon. In addition or instead the non-hydrocarbon gases may comprise one or more chemical compounds or species that were originally comprised by the process gas and which are substantially unchanged.

The method may comprise returning separated one or more chemical species originally comprised by the process gas to the liquid medium and subjecting the separated chemical species to ultrasonic energy in the liquid medium. Alternatively or in addition the method may comprise returning any gases and/or liquids that are not required to be extracted from the apparatus to the liquid medium, so that they can be exposed to ultrasonic energy in the liquid medium.

Optionally, introducing process gas into a liquid medium comprises introducing process gas into a column of a gas lift pump apparatus and causing pumping of liquid medium through the column by gas lift, whereby launching ultrasonic energy generated by the generator into the liquid medium comprises launching ultrasonic energy into liquid medium in the column whereby process gas passing through the column is exposed to ultrasonic energy.

The process gas may comprise carbon dioxide.

The process gas may comprise at least about 10% carbon dioxide by volume.

Optionally the process gas may comprise at least about 14% carbon dioxide by volume, further optionally at least about 20%, still further optionally at least about 40%, still further optionally at least about 50% carbon dioxide by volume.

The process gas may consist essentially of carbon dioxide.

The method may comprise separating hydrocarbon gas from other gas that has passed through the column. Optionally, the method comprises separating methane gas from other gas that has passed through the column.

The method may comprise separating one or more other chemical species such as oxygen gas from other gas and liquid that has passed through the column.

The method may comprise drawing liquid medium into the column from a liquid storage tank.

The liquid may be provided with particles of a catalyst material suspended, dissolved or otherwise dispersed therein.

Optionally the method comprises providing particles of catalyst material suspended, dissolved or otherwise dispersed in the liquid, wherein the catalyst particles comprise iron, optionally iron oxide, optionally a hematite-bearing compound, optionally wherein the catalyst particles consist substantially of hematite.

In some embodiments, the catalyst material may comprise CdSe. The apparatus may comprise means for exposing the catalyst material to visible light, optionally light with a wavelength in excess of about 420 nm, to promote conversion of carbon dioxide to one or more hydrocarbon compounds. The CdSe may act as a photocatalyst to promote conversion of $CO_2$. The CdSe may act in combination with cavitation in collapsing bubbles to promote conversion of carbon dioxide to one or more hydrocarbons. The catalyst material may in some embodiments be in the form of a $CdSe/Pt/TiO_2$ heterostructure catalyst, such as that described in Wang et al, J. Phys. Chem. Lett. 2010, 1, 48-53, the content of which is hereby incorporated herein by reference. Other catalyst materials may also be useful in addition or instead.

In a further aspect of the invention for which protection is sought there is provided apparatus for converting a process gas to one or more other gases, comprising:
  means for introducing process gas into a column of a gas lift device; and
  an ultrasonic energy generator arranged to generate ultrasonic energy in response to a flow of a drive gas therethrough,
  the apparatus being configured to launch ultrasonic energy generated by the generator into the liquid medium such that process gas is subjected to ultrasonic energy,
  the apparatus being arranged to allow collection of process gas that has been exposed to ultrasonic energy.

In another aspect of the invention for which protection is sought there is provided a method of converting a process gas comprising carbon dioxide to one or more hydrocarbons, optionally including methane, comprising:
  introducing process gas into a column of a gas lift pump to cause pumping of liquid medium in the column by gas lift; and
  generating ultrasonic energy by means of an ultrasonic energy generator by driving a drive gas therethrough, the method comprising launching ultrasonic energy generated by the ultrasonic energy generator into liquid medium in the column, whereby process gas passing along the column is subjected to ultrasonic energy generated by the generator,
  the method further comprising capturing gas that has passed through the column.

The method may comprise generating oxygen gas in addition to one or more hydrocarbons.

Gas that has passed through the column may be subject to separation whereby one or more product chemical species generated at least in part by ultrasonic irradiation of process gas are separated from the gas that has passed through the column. The one or more product chemical species may include a hydrocarbon such as methane.

In another aspect of the invention for which protection is sought there is provided apparatus for converting carbon dioxide to one or more hydrocarbons, e.g. methane, and/or oxygen, comprising:
  means for bubbling carbon dioxide in or through a liquid medium; and
  means for exposing carbon dioxide bubbles in the liquid medium to ultrasonic energy,
  the apparatus being arranged to allow collection of gas that has been exposed to ultrasonic energy.

The apparatus may comprise a whistle device operable to generate the ultrasonic energy by passage of gas therethrough. The apparatus may be arranged to pass carbon dioxide through the whistle device to generate the ultrasonic energy.

The gas may be released into the liquid medium following passage through the whistle device. Alternatively the gas may be recirculated through the whistle device. Still further alternatively the gas may be vented to the atmosphere. Optionally the gas may be stored in storage means such as a storage vessel.

The apparatus may be arranged to generate microbubbles of carbon dioxide in the liquid medium by means of a microbubble generator, and to expose the microbubbles to ultrasonic energy. Exposure of the microbubbles to ultrasonic energy may be arranged to result in the conversion of carbon dioxide to at least methane and oxygen.

The reaction may be represented by the following equation:

$$CO_2 + 4H_2O = CH_4 + 2H_2O + 2O_2$$

or, alternatively, $$CO_2 + 2H_2O = CH_4 + 2O_2.$$

In an aspect of the invention for which protection is sought there is provided apparatus for converting carbon dioxide to one or more hydrocarbons, e.g. methane, and/or oxygen, comprising:
means for bubbling carbon dioxide through a liquid medium; and
means for exposing carbon dioxide bubbles in the liquid medium to ultrasonic energy,
the apparatus being arranged to allow collection of chemical species that have been exposed to ultrasonic energy. The chemical species may be in the form of liquid(s) and/or gas(es).

In another aspect of the invention for which protection is sought there is provided apparatus for converting carbon dioxide to one or more hydrocarbons (e.g. including methane) and/or oxygen, comprising:
means for exposing gas comprising carbon dioxide to ultrasonic energy, and
means for collecting gas that has been exposed to ultrasonic energy.

The ultrasonic energy may be generated by an ultrasonic whistle device.

In a further aspect of the invention for which protection is sought there is provided apparatus for converting carbon dioxide to one or more hydrocarbons (e.g. including methane) and/or oxygen, comprising:
a gas lift column through which a liquid medium may be pumped by gas lift, and
a fluid delivery device for delivering a flow of a carbon dioxide fluid into the column,
the apparatus comprising a device for generating ultrasonic energy by the flow of carbon dioxide therethrough, the device being operable to launch the ultrasonic energy into the liquid medium in the column thereby to subject the carbon dioxide to ultrasonic energy,
the apparatus further comprising means for capturing gas that has passed through the column.

The device for generating ultrasonic energy may comprise a whistle device operable to generate the ultrasonic energy by passage of gas therethrough. The apparatus may be arranged to pass carbon dioxide through the whistle device to generate the ultrasonic energy. The gas may be released into the liquid medium following passage through the whistle device.

Alternatively, gas passing through the whistle device may be re-pressurised and forced through the whistle device again. It is to be understood that in some embodiments gases other than carbon dioxide may be passed through the whistle device in addition to or instead of carbon dioxide.

The apparatus may be arranged to generate microbubbles of gas containing or consisting substantially of carbon dioxide in the liquid medium by means of a microbubble generator, and to expose the microbubbles to ultrasonic energy. Experiments demonstrate that exposure of the microbubbles containing carbon dioxide to ultrasonic energy under suitable conditions may result in the conversion of carbon dioxide to methane and oxygen.

The microbubbles may advantageously be formed to have a diameter in the range of about 50 microns or less. The microbubbles may be formed to have a diameter in the range of about 1 micrometer to about 50 micrometers.

In another aspect of the invention for which protection is sought there is provided gas conversion apparatus for converting a process gas to one or more other gases, comprising:
means for introducing process gas into a liquid medium; and
an ultrasonic energy generator arranged to generate ultrasonic energy,
the apparatus being configured to launch ultrasonic energy generated by the generator into the liquid medium such that process gas is exposed to ultrasonic energy,
the apparatus being arranged to allow collection of process gas that has been exposed to ultrasonic energy.

In a further aspect of the invention for which protection is sought there is provided apparatus for converting carbon dioxide to one or more hydrocarbons (e.g. including methane) and/or oxygen, comprising:
a gas lift column through which a liquid medium may be pumped by gas lift, and
a fluid delivery device for delivering a flow of a carbon dioxide fluid into the column,
the apparatus comprising a device for generating ultrasonic energy, the device being operable to launch the ultrasonic energy into the liquid medium in the column thereby to subject the carbon dioxide to ultrasonic energy,
the apparatus further comprising means for capturing and/or containing gas that has passed through the column.

The gas may be contained in an ullage space of a liquid tank in some embodiments, at least initially following passage through the column. Alternatively or in addition the gas may be fed directly from the column to a separate storage or processing volume, optionally through a separator. In some embodiments the column may be coupled to or extend to form a conduit through which gas passing along the conduit is conveyed to a storage or processing volume.

Optionally, the device for generating ultrasonic energy is configured to generate ultrasonic energy by the flow of gas therethrough.

Constituting a yet further aspect of the invention for which protection is sought are certain constructions of bubble generator per se for use in embodiments of gas conversion apparatus of any of the above-defined aspects of the invention, as well as in other treatment apparatuses such as various gas lift pump apparatuses, e.g. for circulation of liquid in a liquid storage or ballast tank of a vessel.

Accordingly, in another aspect of the invention for which protection is sought there is provided a bubble generator for generating bubbles, preferably microbubbles, of a gas in a liquid medium in a treatment apparatus, the bubble generator comprising:

a bubble forming portion for location in the liquid medium and configured for forming bubbles of the gas therein;

an input portion for delivering an input flow of the gas to the bubble forming portion; and an output portion for emitting an output flow of the formed gas bubbles from the bubble forming portion;

wherein the bubble forming portion comprises one or more vortex-inducing elements configured for inducing a vortex in a flow of gas therethrough.

In a further aspect of the invention for which protection is sought there is provided a bubble generator for generating bubbles, preferably microbubbles, of a gas in a liquid medium in a treatment apparatus, the bubble generator comprising:

a vortex-inducing portion;

an input portion for delivering an input flow of the gas to the vortex-inducing portion; and an output portion for emitting an output flow of gas bubbles;

wherein the vortex-inducing portion comprises one or more vortex-inducing elements configured for inducing a vortex in a flow of gas therethrough.

In some embodiments of the above-defined bubble generator the one or more vortex-inducing elements may comprise one or more, preferably a plurality of, vortex-inducing blade elements located within a gas flowpath between the input portion and the outlet portion. The or each blade element preferably includes an impingement face and the impingement face of the or each blade element may preferably be oriented so as to be non-parallel to a direction of input gas flow in the input portion. In this manner the input flow of gas impinging on the impingement face(s) of the blade element(s) is forced to change direction as it flows onto and past the blade element(s), thereby creating a swirling or vortex effect in the gas flowpath as it flows from the input portion to the output portion.

In some embodiments of the above-defined bubble generator a plurality of blade elements may be provided and they may preferably be equi-spaced relative to each other, especially in a circular arrangement, around a longitudinal axis normal to a direction of input gas flow in the input portion.

In some embodiments of the above-defined bubble generator the vortex-inducing portion may comprises a dome member for channelling gas flowing into the vortex-inducing portion towards the vortex-inducing element(s). In a preferred form the dome member may have a radiused internal shape configured for reducing the generation of eddy currents as gas flows in the gas flowpath therewithin.

In some embodiments of the above-defined bubble generator there may be further provided therein an accelerator portion downstream of the one or more vortex-inducing elements for accelerating the output flow of the gas, especially in a direction towards an outlet of the output portion where the flow of gas enters the liquid medium in the apparatus. The accelerator portion may for example define a portion of the gas flowpath which comprises a conical passageway having an internal shape which tapers radially inwardly towards its outlet. In this manner the vortex or swirling flow of the gas may be enhanced, thereby improving the degree of cavitation of the bubbles of the gas in the liquid medium, especially—in preferred practical embodiments—upon their exposure to ultrasonic energy provided by the one or more ultrasonic energy generator(s) which may also be present.

In some practical embodiments of the above-defined bubble generator the input portion for delivering an input flow of the gas to the vortex-inducing portion may comprise a conduit mounted in the apparatus via a proximal end thereof, e.g. in the manner of a cantilevered-type fixing, and carrying the vortex-inducing portion at a distal end thereof. The conduit may support the vortex-inducing portion in a liquid medium away from a sidewall of the apparatus such as a sidewall of a storage tank, pipeline, or column of a gas lift pump apparatus, optionally within the column of the gas lift pump apparatus. To assist the supporting of the conduit, especially given that flow of liquid medium in or through the apparatus may exert relatively high forces on the exterior of the conduit, the mounting of the conduit in the apparatus may be enhanced by one or more support members or webs, e.g. one or more strengthening webs, brackets, buttresses or like elements or members provided between the conduit and its anchoring location on or in the apparatus. In some embodiments a direction of gas flow in the conduit and a direction of flow of liquid past the input portion may be oriented substantially perpendicular to one another.

In preferred embodiments of the above-defined bubble generator per se it is preferably a generator of microbubbles, which preferably means it is constructed and arranged to generate gas bubbles of a diameter in the range of about 50 microns or less. The bubble generator may be configured to generate bubbles of a diameter in the range from about 1 micron to about 50 microns, optionally in the range from about 10 microns to around 50 microns, further optionally in the range from about 20 microns to about 50 microns.

Further advantageous features of embodiments of a bubble generator according to this alternative aspect of the invention will be described further below in connection with certain specifically described embodiments of other aspects of the invention.

Embodiments of the above-defined bubble generator per se of this alternative aspect of the invention may be put to various uses in a variety of treatment apparatuses. In some preferred applications the treatment apparatus may be a gas conversion apparatus and the gas is a process gas for conversion to one or more other gases by the apparatus. Such gas conversion apparatus may be a gas conversion apparatus according to various embodiments of the present invention in its various aspects as defined hereinabove.

However in other applications the treatment apparatus may be a gas lift pump apparatus, for example a gas lift pump apparatus for use in, or when used in, a liquid storage or ballast tank of a vessel such as a ship or other sea-going or waterborne craft, e.g. for circulation of water or other liquid therein in a process for the killing of bacterial or non-bacterial aquatic nuisance species (ANS).

Thus, according to another alternative aspect of the invention for which protection is sought there is provided a gas lift pump apparatus comprising:

a column having in use a substantially upright portion through which a liquid medium may be pumped by gas lift; and a bubble generator according to another aspect of the invention for generating bubbles of the gas in the liquid medium.

Optionally the apparatus may comprise a gas delivery device for delivering a flow of a gas into the column at a first location of the column to cause liquid medium to be pumped by gas lift.

The bubble generator may be arranged to cause bubbles to be formed in liquid medium as it passes through the column. Alternatively the bubble generator may be arranged to cause bubbles to be formed in a liquid medium which is then supplied to the column.

In preferred embodiments of the above-defined gas lift pump apparatus there may further be provided at least one ultrasonic energy generator configured for applying ultrasonic energy to gas bubbles formed by the bubble generator. Such one or more ultrasonic energy generators may be any of those defined herein in connection with embodiments of the other aspects of the invention as applied to gas conversion apparatuses.

The gas lift pump apparatus may be comprised by, or constitute at least a portion of, a ballast water treatment apparatus. The apparatus may be provided onboard a vessel. The apparatus may be configured to treat ballast water of one or more ballast tanks. The apparatus may be configured to generate microbubbles in the ballast water and, optionally, expose the microbubbles in the ballast water to ultrasonic energy. The microbubbles may comprise ships flue gas, optionally a combustion gas, and comprise carbon dioxide. The gas employed by the microbubble generator to generate microbubbles may have an oxygen concentration of less than 2%, optionally less than 1.5%, further optionally less than 1%. The oxygen concentration may be greater than 0.1% the oxygen concentration may be around 0.5% or around 0.6% in some embodiments.

In preferred embodiments of the above-defined gas lift pump apparatus the bubble forming portion of the bubble generator may advantageously be positioned substantially coaxially within the column.

Embodiments of the above defined gas lift apparatus may take a wide variety of forms. Some particular useful forms are those as disclosed and illustrated in our co-pending International Patent Application WO2013/093527, the entire contents of the specification and drawings of which published application are hereby implicitly incorporated herein by reference thereto.

Within the scope of this application it is expressly envisaged that the various aspects, embodiments, examples and alternatives set out in the preceding paragraphs, in the claims and/or in the following description and drawings, and in particular the individual features thereof, may be taken independently or in any combination. Features described in connection with one embodiment are applicable to all embodiments, unless expressly stated otherwise or such features are incompatible.

BRIEF DESCRIPTION OF THE DRAWINGS

Various embodiments of the invention in its various aspects will now be described, by way of example only, with reference to the accompanying drawings, in which:

FIG. 3 is a schematic illustration of an array of ultrasonic generators employed in the apparatus of FIG. 1 in (a) side view and (b) as viewed along a direction of flow of fluid along a column of the apparatus;

FIG. 7 shows an ultrasonic generator of the embodiment of FIG. 5;

FIG. 8 is an enlarged view of a nozzle member of the embodiment of FIG. 7 in (a) side view, (b) a view along direction V1 of (a), and (c) a section view along line B-B of (b);

DETAILED DESCRIPTION OF EMBODIMENTS

Figure 1:
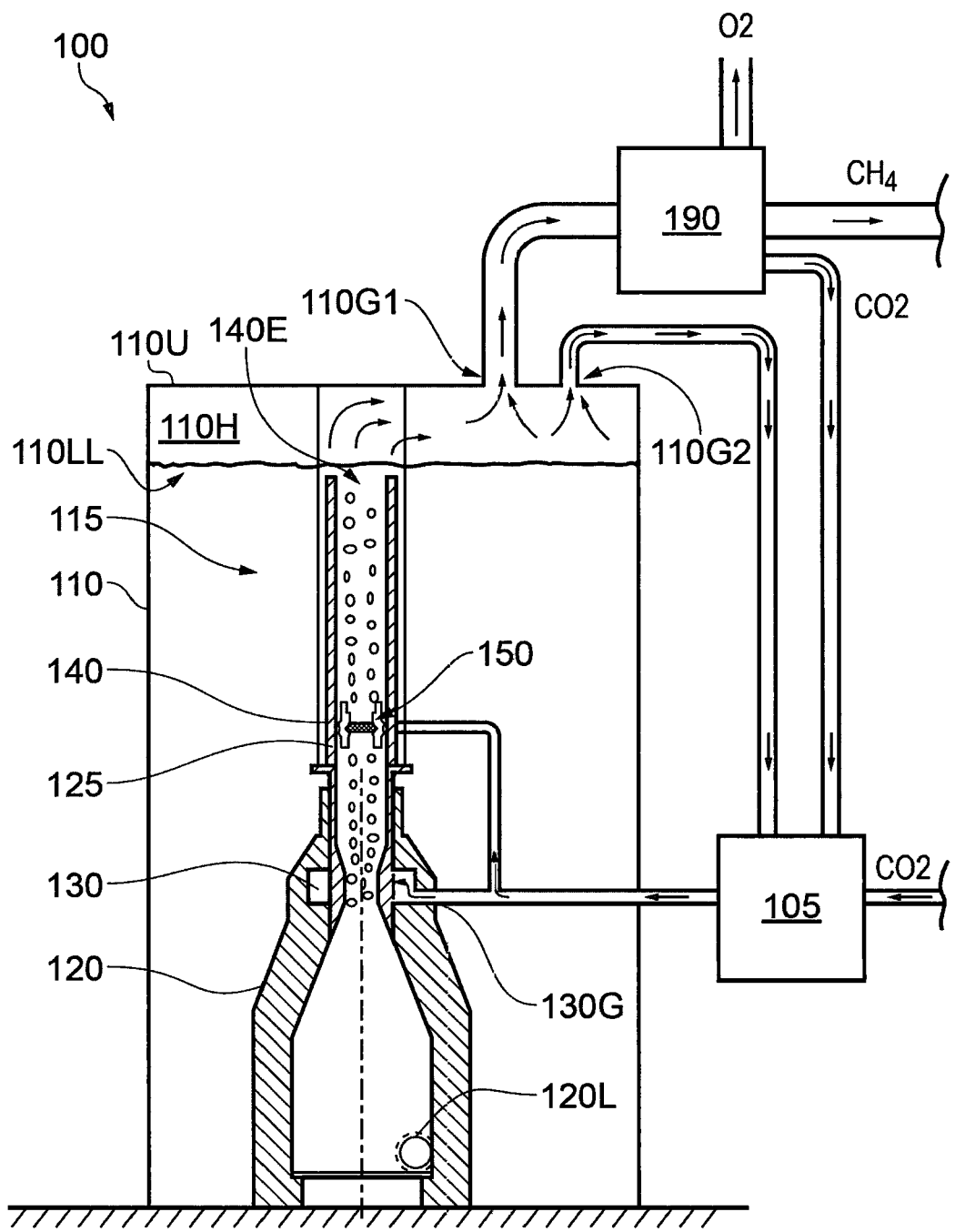
FIG. 1 is a schematic illustration of an apparatus according to an embodiment of the present invention.

FIG. 1 is a schematic illustration of a gas conversion apparatus 100 according to an embodiment of the present invention. The apparatus 100 of FIG. 1 is configured to convert a carbon dioxide process gas into methane gas and oxygen gas.

The apparatus 100 has a compressor 105 for compressing carbon dioxide process gas supplied to the apparatus 100 from an external source. Process gas that has been compressed by the compressor 105 is supplied to a converter portion 115 of the apparatus 100 that is located within a liquid holding tank 110. The tank 110 contains a sufficient amount of water to substantially immerse the converter portion 115. Liquids other than water may also be useful. The liquid may contain one or more additives in order to promote gas conversion, inhibit corrosion and/or inhibit bacterial growth.

The converter portion 115 has a microbubble generator portion 120 connected to an upright conduit or column 125. The microbubble generator portion 120 is configured to receive carbon dioxide process gas at a gas inlet 130G and liquid from the tank 110 at a liquid inlet 120L. As described in more detail below, the microbubble generator portion 120 generates microbubbles and allows them to rise upwardly into the column 125.

The column portion 125 is provided with an ultrasonic generator portion 140 in a lower part thereof. The ultrasonic generator portion 140 has an array of whistle devices 150 that generate ultrasonic energy when pressurised gas is forced through them. The ultrasonic energy causes cavitation of microbubbles rising through the column portion 125, resulting in conversion of at least some carbon dioxide to methane and oxygen.

Gas in the column rising through the ultrasonic generator portion 140 is exhausted from the column 140 at a free end 140E thereof, and rises to a headspace 110H of the tank 110 above a level of liquid 110LL in the tank 110. A mixture of methane, oxygen and unconverted carbon dioxide therefore collects in the headspace 110H. In some embodiments, one or more other hydrocarbons may collect in the headspace 110H in addition or instead.

The tank 110 has first and second gas outlet ports 110G1, 110G2 that connect to the tank 110 through an upper wall 110U of the tank 110 at a level above a maximum expected level of liquid in the tank 110 in use.

First gas outlet port 110G1 is coupled to a gas separator portion 190 whilst second gas outlet port 110G2 is coupled to an inlet of compressor 105. Gas passing out from the tank 110 via the second gas outlet port 110G2 is therefore recirculated through the converter portion 115. This feature enables a concentration of carbon dioxide in the headspace 110H to be reduced, thereby reducing the amount of gas from the headspace 110H that must be processed by the separator 190 in order to obtain a given amount of methane. The relative amounts of gas that flow from the headspace 110H to the compressor 105 and separator 190 may be controlled in order to control the concentration of carbon dioxide and one or more other gases in the headspace 110H.

Microbubble Generator

The microbubble generator portion 120 of the apparatus 100 of FIG. 1 is a cyclone (or 'cyclonic') microbubble generator 120. It is arranged to induce swirl in liquid passing into a bubble shear portion 130 of the generator 120. Swirl is induced in order to promote formation of microbubbles in liquid passing through the bubble shear portion 130.

Figure 2A:
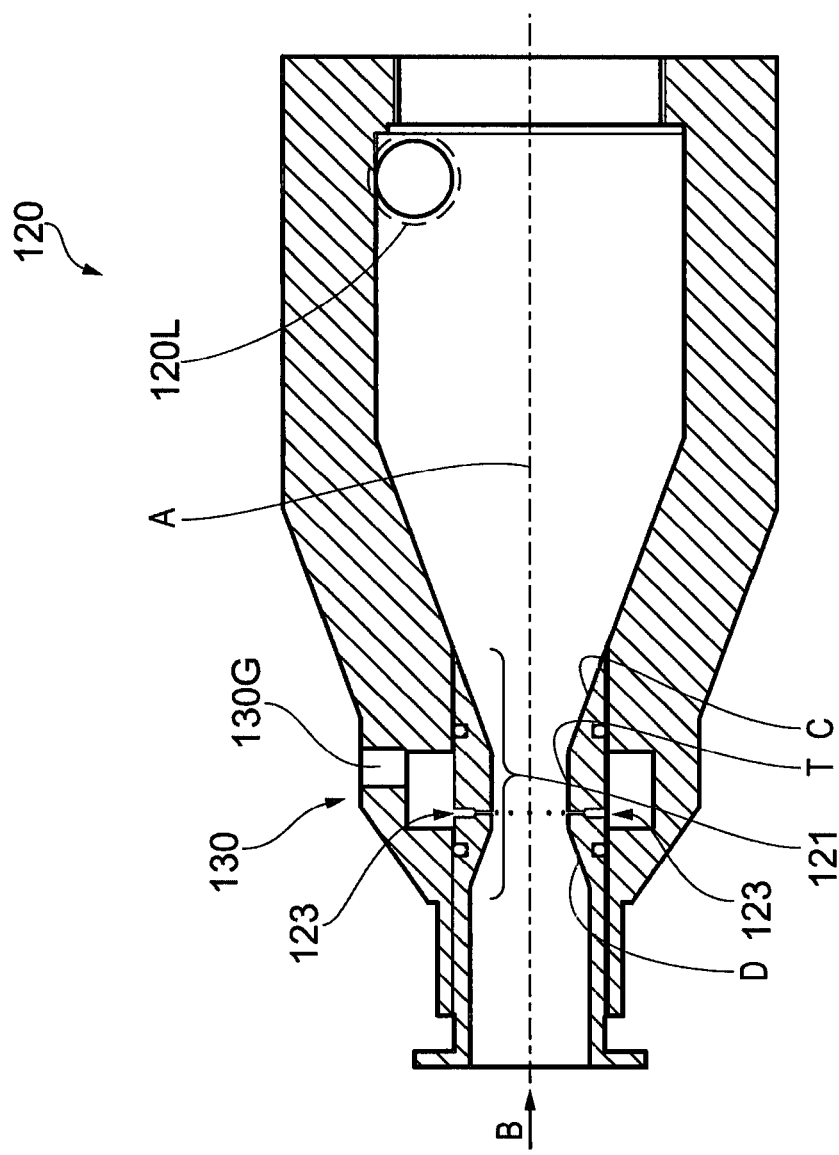
FIG. 2 is a schematic illustration of a microbubble generator according to an embodiment of the present invention in (a) cross-sectional view along a substantially horizontal axis and (b) as viewed down a column of the apparatus.
Figure 2B:
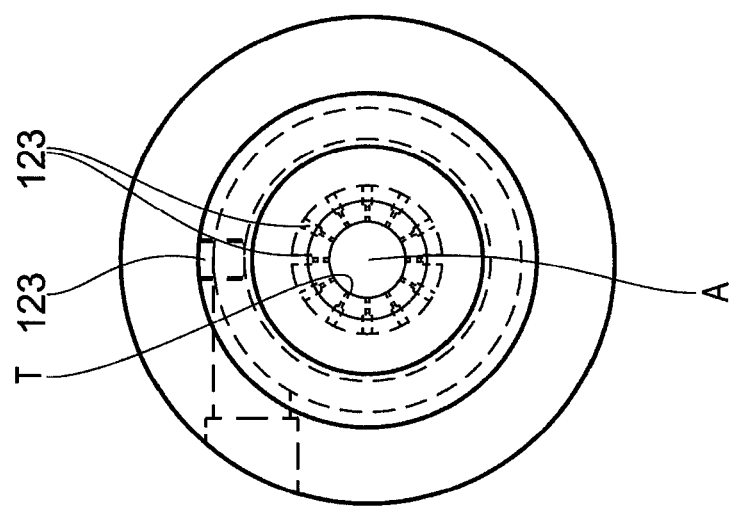

The microbubble generator portion 120 is shown in further detail in FIG. 2. FIG. 2(a) is a cross-sectional view of the generator portion 120 as viewed normal to a cylinder axis A of the microbubble generator portion 120. FIG. 2(b) is a view along the cylinder axis A as viewed along the direction of arrow B.

The generator portion 120 is provided with a liquid inlet 120L for allowing liquid in the tank 110 to flow into the converter portion 115. As can be seen from FIG. 2(a), liquid entering the generator portion 120 through inlet 120L does so in a direction substantially tangential to an inner wall of the generator portion 120. This feature promotes swirl flow of liquid through the generator portion 120.

Liquid flowing through the microbubble generator portion 120 is forced to flow through a choke or Venturi portion 121. The Venturi portion 121 has a converging portion C being a portion over which a cross-sectional area of the generator portion 140 decreases with distance from the liquid inlet 120L, a throat portion T of substantially constant cross-sectional area immediately downstream of the converging portion C, and a diverging portion D of increasing cross-sectional area immediately downstream of the converging portion C.

Gas inlets 123 are provided in the throat portion T of the Venturi portion 121 and are arranged to allow process gas to be injected into liquid passing through the throat portion T. The inlets 123 are provided at spaced apart locations around a circumference of the throat portion T, neighbouring inlets 123 being substantially equidistant from one another. In the embodiment shown twelve inlets 123 are provided. Other numbers of inlets 123 and other arrangements of inlets 123 may also be useful.

In use, liquid passing through the Venturi portion 121 is arranged to cause shear of gas bubbles forming in liquid passing through the generator portion 120. The bubbles form as gas is injected through the inlets 123. Shear of the bubbles causes a reduction in size of the bubbles compared with an equilibrium size of gas bubbles formed in stagnant liquid. A microbubble generator portion 120 of the type shown in FIG. 2 has been found to be highly effective in producing a stable flow of microbubbles in the converter portion 115.

Ultrasonic Energy Generator

The converter portion 115 is configured in use to deliver a flow of liquid with microbubbles of process gas entrained therein from the microbubble generator portion 120 to the ultrasonic generator portion 140.

The ultrasonic generator portion 140 is shown in more detail in FIG. 3. FIG. 3(a) shows the ultrasonic generator portion 140 in side view whilst FIG. 3(b) shows the ultrasonic generator portion 140 as viewed along axis A from above. The ultrasonic generator portion 140 includes two linear arrays of whistle devices 141AA, 141AB, respectively. Each array has four pairs of whistle devices 141, one device of each pair being mounted above a substantially horizontal gas feed line GA, GB whilst the other is mounted below it. Gas flowing along each feed line GA, GB is forced to flow through the whistle devices 141, the gas being exhausted to liquid within the column 125.

Figure 4A:
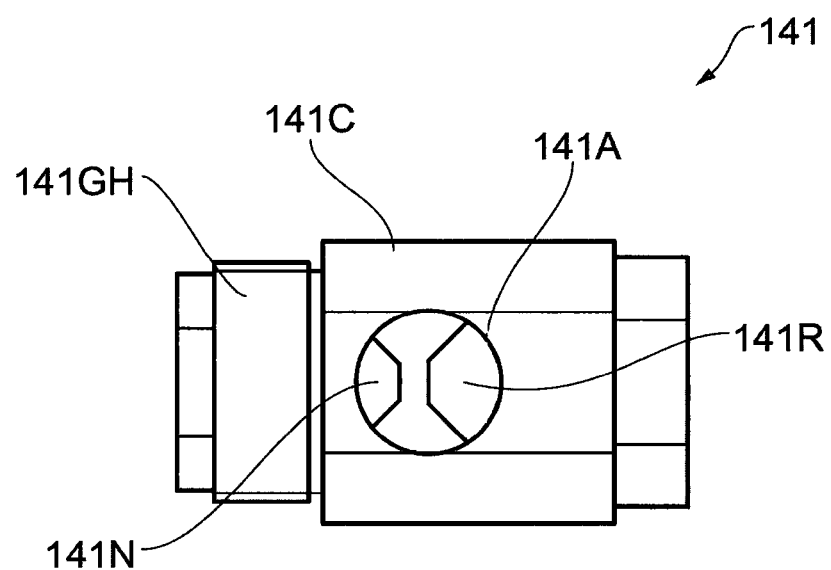
FIG. 4 shows (a) a side view of a whistle device suitable for use in apparatus according to an embodiment of the invention and (b) a cross-sectional view along the same viewing direction as in (a)
Figure 4B:
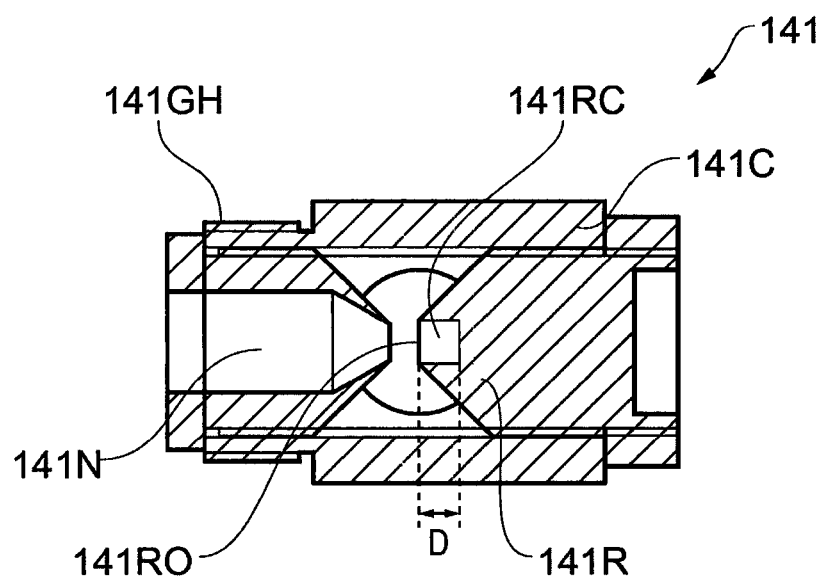

With reference to FIG. 4, each whistle device 141 has a portion in the form of a chamber 141C that also provides a whistle body. A nozzle member 141N and a receptor member 141R are coupled to the whistle body 141C. The whistle body 141C is arranged to support the receptor member 141R in a substantially fixed spaced apart and substantially coaxial relationship with the nozzle member 141N. The nozzle member 141N is shown coupled to a gas supply head 141GH that forms part of the respective gas feed line GA, GB.

The nozzle member 141N is arranged to direct a flow of process gas through an opening 141RO of the receptor member 141R into an open cavity 141RC defined by the receptor member 141R. The receptor member 141R is arranged to be screwed into a tapped aperture in the whistle body 141C thereby to couple the receptor member 141R to the whistle body 141C. The receptor member 141R is thus arranged to close one end of the chamber 141C. Flow of gas from the nozzle member 141N to the cavity 141RC results in the generation of ultrasonic energy in the manner of a Hartmann-type whistle device. Other whistle devices may also be useful.

A distance between the opening 141RO of the receptor member 141R and nozzle 141N may be adjusted by means of the screw thread by rotation of the receptor member 141R.

In some arrangements a depth D of the cavity 141RC defined by the receptor member 141R may be adjusted. In some arrangements the adjustment is by means of a further screw adjustment, for example by adjusting a position of a screw defining at one end an interior basal surface of the cavity 141RC. This feature has the advantage that an amount of sound energy produced by the device 141 may be optimised. A frequency of sound energy (i.e. a frequency of sound waves generated by the device 141) may be adjusted by adjustment of the depth D in some embodiments.

The whistle body 141C provides a substantially tubular sleeve coaxial with the nozzle member 141N and receptor member 141R, the sleeve having a pair of apertures 141A formed therein to accommodate flow of gas from the nozzle member 141N out from the body 141C and into liquid in the column 125. The whistle devices 141 thereby act as gas delivery devices, delivering a flow of gas into liquid in the column. The gas rises in the liquid, causing pumping of liquid through the converter portion 115 by gas lift.

The gas used to drive the ultrasonic generator may be referred to as a drive gas. The drive gas may be of the same type and optionally from the same source as the process gas. Alternatively the drive gas may be a different gas.

In some embodiments, the process gas may be the product of a combustion reaction. The process gas may comprise around 13-14% carbon dioxide or other amount depending on the combustion conditions, the balance being nitrogen, sulphur oxides ($SO_x$), and nitrous oxides ($NO_x$). For example the process gas may be delivered from a coal, oil or gas-fired powerstation. In some embodiments the process gas may be ship's flue gas. Other sources of gas containing carbon dioxide are also useful such as exhaust gas from an internal combustion engine.

In some alternative embodiments, the apparatus is arranged such that drive gas is not exhausted into liquid in the column. In some embodiments the drive gas may be repressurised and recirculated through the whistle devices 141.

Conversion Reaction

It is understood that exposure of microbubbles of carbon dioxide to ultrasonic energy in the column 125 of the converter portion 110 causes the bubbles to collapse, causing rapid and extreme heating of the gas and the generation of free radicals. This is believed to result in the conversion of carbon dioxide to methane and oxygen by the equation below.

The reaction may be represented by the following equation:

$$CO_2 + 4H_2O = CH_4 + 2H_2O + 2O_2$$

or, alternatively, $$CO_2 + 2H_2O = CH_4 + 2O_2.$$

In some embodiments, a catalyst may be provided for catalysing the reaction. The catalyst may be provided in particulate form, particles of catalyst being suspended in liquid medium in the tank 110. In some embodiments, the catalyst particles contain iron or an oxide thereof. Particles of hematite or a hematite-bearing particle are useful in some embodiments.

Embodiments of the present invention have the feature that one or more gases that may be harmful to the environment such as carbon dioxide may be converted to useful forms in a relatively straightforward manner and by means of an energy efficient process. The generation of ultrasonic energy by means of a flow of pressurised gas enables a relatively robust and resilient apparatus to be provided compared with other methods of generating ultrasonic energy, such as electrical transducer devices.

Embodiments of the present invention are useful in converting carbon dioxide present in combustion gases emitted by power stations to be converted into oxygen and methane gas. Oxygen gas generated in some embodiments of the present invention may be released to the environment or stored in oxygen gas containers and used or sold, for example as an industrial process gas.

The methane gas generated may be used as a fuel, or for any other suitable purpose such as in processing of chemicals.

It is to be understood that in some embodiments, recirculation of gas that has passed through the column 125 is not performed. In some embodiments, the gas is supplied to the separator 190 without recirculation. In some embodiments gas that has passed along the column 125 is not delivered to a separator 190. In some embodiments the gas is stored in a storage tank.

It is to be understood that gas conversion apparatus according to some embodiments of the present invention may be operated by means of electrical energy generated by a renewable energy source such as solar energy. It is to be understood that in some embodiments, process gas may be supplied to the apparatus at a pressure sufficiently high to enable whistle devices of the ultrasonic energy generator to be operated without a requirement to compress the process gas, such that compressor 105 is not required. Furthermore, the process gas may be supplied at a pressure sufficiently high to enable powering of a compressor for compressing gas undergoing recirculation through the column 125 after being drawn from the head space 110H, such that little or substantially no additional power is required to operate the compressor 105.

In some embodiments, gas collecting in the head space 110H, being a mixture of methane and oxygen at least, in some embodiments, may be in a form that may be used as a fuel or in an industrial process without a requirement to separate methane and oxygen. In embodiments in which residual carbon dioxide process gas is present in the head space 110H, the concentration of carbon dioxide may be reduced by recirculation of gas through the compressor 105 until the concentration is sufficiently low that the gas is useful as a fuel or in a particular industrial process. Other arrangements may also be useful.

In some alternative embodiments of the present invention, a different microbubble generator and/or a different ultrasonic energy generator may be employed.

One alternative embodiment of the converter portion is shown at 215 in FIG. 5. The converter portion 215 of FIG. 5 has a different microbubble generator 220 and a different ultrasonic energy generator 240. Like features of the embodiment of FIG. 5 to those of the embodiment of FIG. 1 are shown with like reference numerals incremented by 100.

Figure 5A:
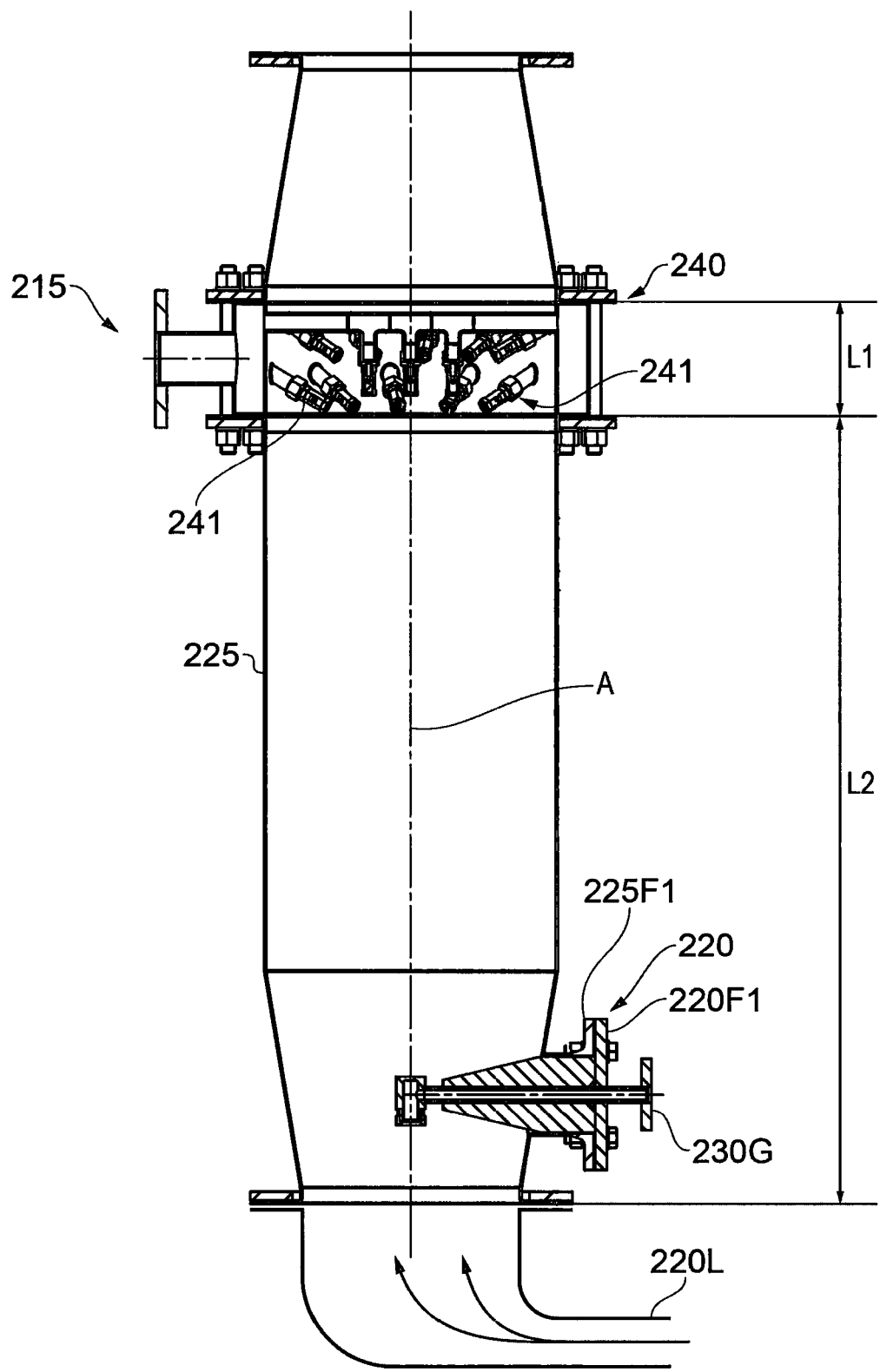
FIG. 5 shows a converter portion according to a further embodiment of the invention, in (a) sectional view and (b) plan view.
Figure 5B:
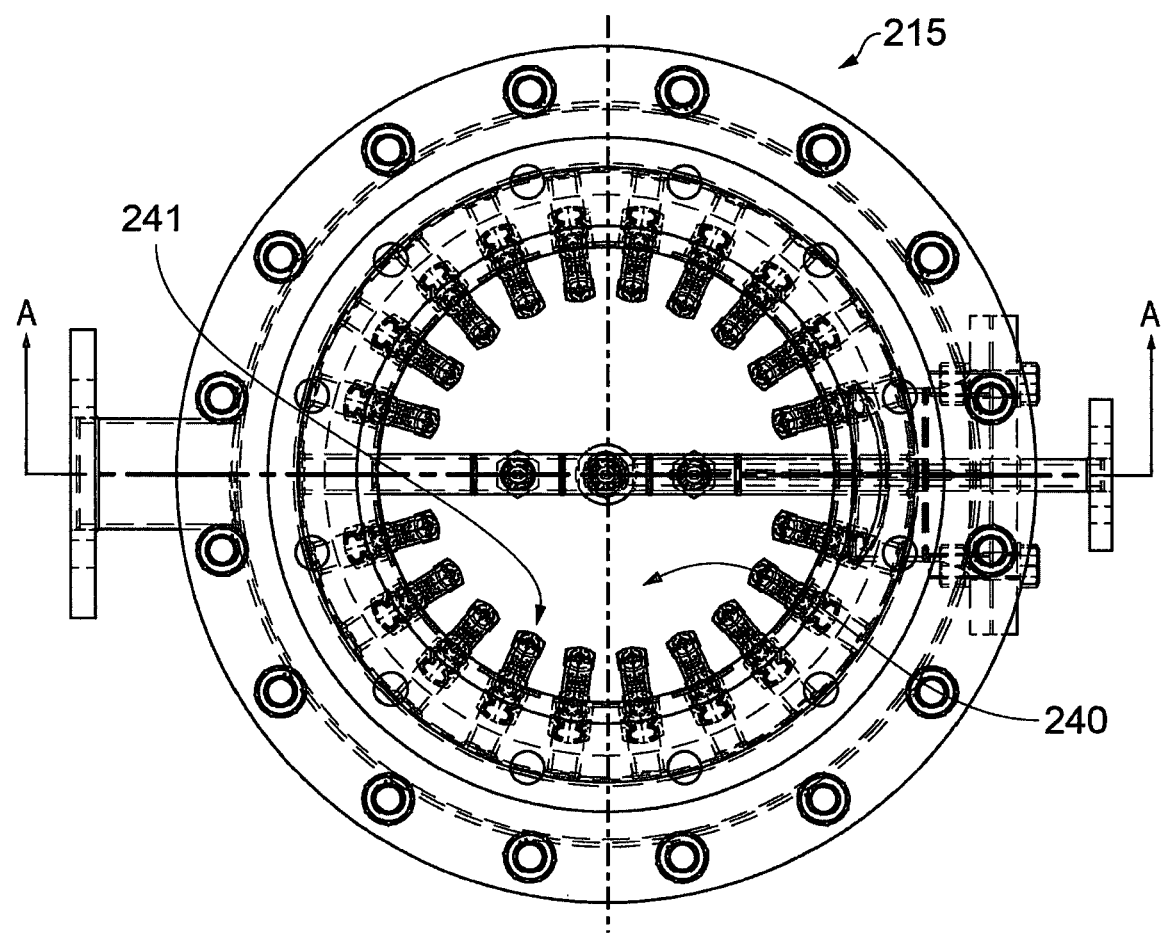

FIG. 5 shows the converter portion 215 as viewed at section A-A of FIG. 5(b). FIG. 5(b) shows the converter portion 215 in plan view. The converter portion 215 has a column 225 that has at its base a liquid inlet 220L arranged to allow liquid to be drawn or pumped into the column from the lower end thereof.

The embodiment of FIG. 5(a) is substantially to scale, with length L1 being around 160 mm and length L2 being around 1100 mm. Other dimensions may also be useful.

The microbubble generator 220 is provided above the inlet 220L and comprises a flange 220F1 arranged to couple the generator 220 to a corresponding flange 225F1 of the column 225. It is to be understood that the column 225 may be disposed in any desired orientation. In the present embodiment the column 225 is disposed in a substantially upright, vertical direction with a cylinder axis A of the column 225 substantially vertical. In the embodiment of FIG. 5 the flange 220F1 of the microbubble generator 220 lies in a substantially vertical plane.

Figures 6A, 6B, 6C:
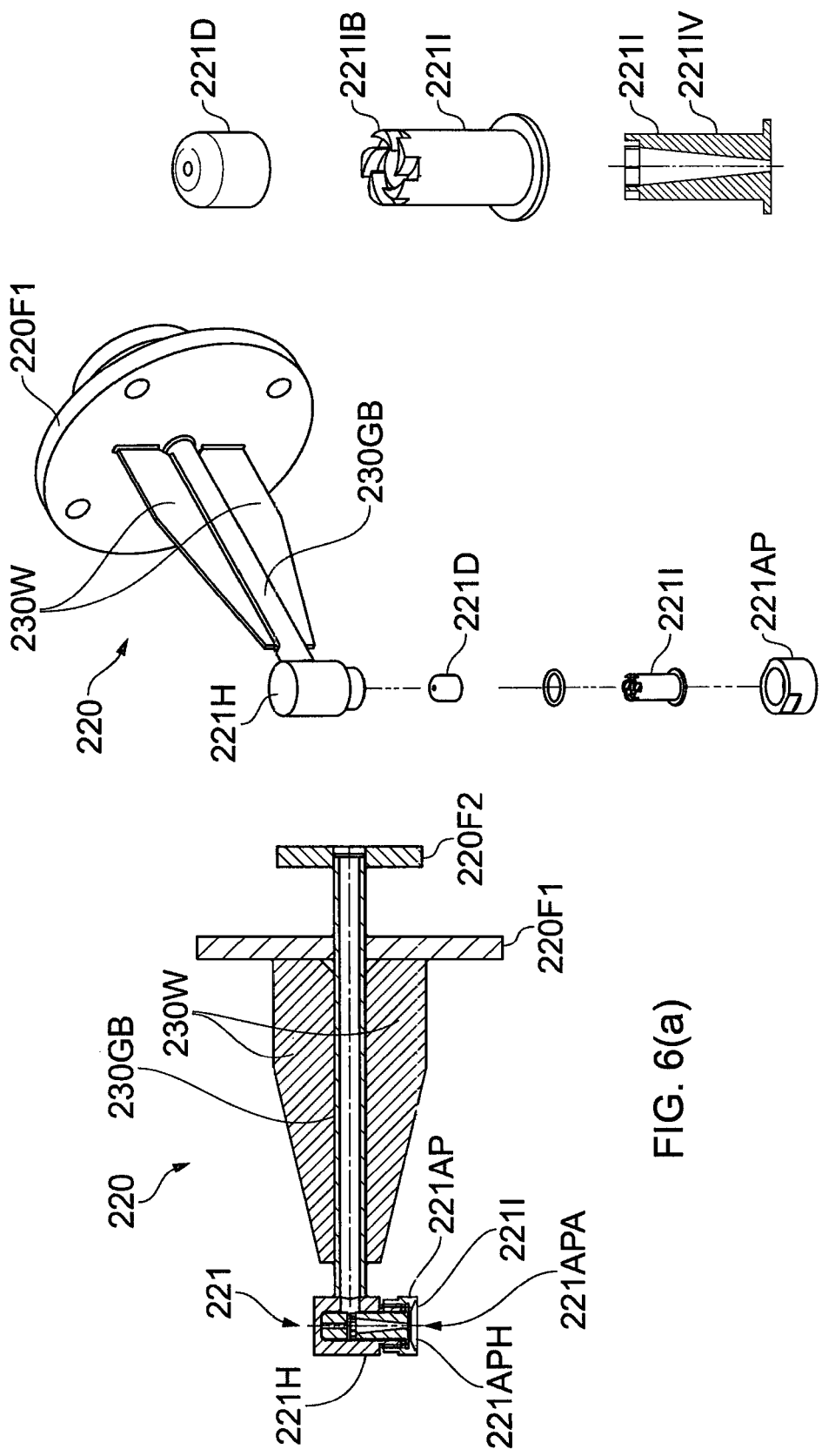
FIG. 6 shows a microbubble generator of the embodiment of FIG. 5.

As shown in FIG. 6(a), the microbubble generator 220 has a gas conduit 230GB that passes through and is fixedly coupled to the flange 220F1. The conduit 230GB extends from the flange 220F1 substantially normal to the flange 220F1 and coaxial therewith, and defines a boom-like structure for supporting a gas bubbler device 221 at a free end of the boom. A pair of upstanding web portions 230W are attached to the flange 220F1 at one end, and run along and are coupled to the conduit 230GB along a substantial portion of a length of the conduit 230GB. The web portions 230W are disposed directly above and below the conduit 230GB, and serve to stiffen and strengthen the conduit 230GB. It is to be understood that flow of liquid past the conduit 230GB within the column 225 may exert a not insubstantial force on the conduit 230GB. The presence of the web portions 230W therefore serves at least in part to reduce bending of the conduit 230GB. The web portions 230W are arranged to be substantially parallel to flow of liquid along a direction parallel to cylinder axis A of the column 225.

The bubbler device 221 has a housing 221H defining a downward-opening cavity in which is provided a hollow dome member 221D being a dome-shaped or cup-shaped member having a radiused internal shapeform. The dome member 221D is disposed above a flow of process gas into the bubbler device 221 and is arranged to assist in channeling gas that flows into the bubbler device 221 downwardly towards insert member 221I as described below. The radiused internal shapeform of the dome member 221D serves to reduce eddy current generation in the housing 221H when process gas flows into the dome member 221D.

Process gas entering the bubbler 221 is caused to flow downwardly through the substantially cylindrical, hollow insert member 221I that is arranged to enjoy a sliding fit within the housing 221H of the bubbler 221, being introduced from below (with respect to the illustrated orientation) during assembly. The insert member 221I is provided with five swirl or vortex-inducing upstanding blade elements 221IB equally spaced around an upper peripheral rim thereof. Other numbers of blade elements 221IB may also be useful. The blade elements 221IB are aligned with a longitudinal cylinder axis of the conduit 230GB such that their impingement faces are positioned directly in a flowpath of process gas passing from the conduit 230GB into the housing 221H. The blade elements 221IB are positioned in a circular symmetrical arrangement around a longitudinal axis normal to the direction of gas flow of the process gas passing from the conduit 230GB into the housing 221H. Process gas entering the bubbler 221 therefore impinges directly on the faces of the blade elements 221IB which causes the process gas to begin to swirl within the bubbler 221. That is, the process gas assumes a vortex-like flowpath. The process gas is forced to flow downwardly through a fluid passage defined by the insert member 221I. The passage is in the form of a cone, being tapered inwardly such that the passage narrows from an upper to a lower end thereof. Consequently, a velocity of process gas flowing downwardly and away from the blade elements 221IB increases as a function of distance from the blade elements 221B.

At the lower end of the insert member 221I a cylindrical aperture cap member 221AP is provided that screws onto the free end of the housing 221H, retaining the insert member 221I within the housing 221H. The aperture cap member 221AP has an aperture 221APA provided in a head portion 221APH thereof, coaxial with the housing 221H. The aperture 221APA is arranged to allow flow of process gas out from the bubbler 221 and into liquid in which the bubbler 221 is immersed. The feature that process gas is caused to assume a swirl flow and subsequently forced to accelerate along the insert member 221I has the feature that gas may be injected into liquid in the column 225 at a relatively high velocity and with high intensity swirl or spin. The present applicant has discovered that gas bubbles formed by injection of gas into liquid in this manner may be caused to be of particularly small size, and less than 50 micrometres in diameter in some embodiments, enabling intimate mixing of the gas with liquid in the column 225. Furthermore, the gas bubbles have been found to be stable and to remain of substantially the same size as they are drawn or forced upwardly towards the ultrasonic energy generator 240 in the flow of liquid upwardly through the column 225.

In the embodiment of FIG. 6, the bubbler 221 is provided substantially coaxially of the column 225 such that a cylinder axis thereof (being substantially coincident with the cylinder axes of the insert member 221I and aperture cap 221AP), is substantially coincident with that of the column 225. Other arrangements may also be useful. However, it is found that by disposing the bubbler 221 such that it is substantially centred with respect to the column 225, a relatively homogeneous flow of microbubbles may be established with respect to a cross-sectional area of the column.

FIG. 7 shows the ultrasonic energy generator 240 in further detail. FIG. 7(a) is a 3D view of the generator 240 whilst FIG. 7(b) is an external view of one of nineteen whilst devices 241 that form part of the generator 240. FIG. 7(c) shows the device 241 as viewed along section B-B of FIG. 7(b) whilst FIG. 7(d) is a 3D view of the device 241. Like features of the device of FIG. 7 to that of the device of FIG. 4 are shown with like reference signs incremented by 100.

As can be seen from FIG. 7(a), sixteen of the whistle devices are arranged circumferentially around the column 225 of the converter portion 215 and three are disposed at spaced apart locations along a diameter of the column 225, facing upstream of a direction of flow of liquid through the column 225, in use. Other numbers of whistle devices and other arrangements of whistle devices are also useful. In the embodiment shown the whistle devices 241 are arranged such that substantially all fluid passing along the column 225 passes within 50 mm of a portion of a body of at least one whistle device 241. This is so as to ensure exposure of microbubbles entrained in the fluid to ultrasonic radiation of sufficiently high intensity. Other distances may also be useful.

As per the whistle device 141 of the embodiment illustrated in FIG. 4, the whistle device 241 of FIG. 7 has a chamber 241C that defines a tapped whistle body. A nozzle member 241N and a receptor member 241R are coupled to the whistle body 241C by means of respective screw threads. The receptor member 241R is substantially wholly contained within the whistle body 241C in the embodiment shown, and in a substantially fixed, spaced apart and substantially coaxial orientation with respect to the nozzle member 241N. In the embodiment shown, the nozzle member 241N is integrally formed from the same component as a gas supply head coupling 241GHC. The coupling 241GHC is provided with an internal thread arranged to allow the nozzle member 241N to be coupled to a gas supply head. An external thread allows the nozzle member 241N to be coupled to the whistle body 241C.

FIG. 8 shows the nozzle member 241N and gas supply head coupling 241GHC separated from the housing 241C. FIG. 8 is drawn substantially to scale and in the present embodiment length L1 is 40 mm and diameter DGHC is approximately 31 mm. Other dimensions are also useful.

As shown in FIG. 8, the nozzle member 241N has a flow-splitting vane element which may also be described as a turbulator 241NT. The turbulator 241NT is a substantially flat, rectangular element arranged to divide gas flowing out from the nozzle member 241N into two halves. The presence of the turbulator 241NT has been found to enable tuning of the frequency of ultrasonic energy generated by the whistle device 241 to a substantially constant, reproducible frequency. In some embodiments the frequency is in the range from around 20 kHz to around 30 kHz, optionally in the range from around 20 kHz to around 26 kHz. Other frequencies greater than 30 kHz and/or less than 20 kHz are also useful, in addition or instead. The length LNT of the turbulator 241NT with respect to the longitudinal axis A of the nozzle member 241N (which is substantially coincident with that of the column 125 in use) is approximately 1 mm. Other dimensions are also useful and a suitable value of length of the turbulator 241NT may be determined empirically by the skilled person.

The nozzle member 241N is arranged to direct a flow of gas through the nozzle member 241N into an open cavity 241RC defined by the receptor member 241R. Flow of gas from the nozzle member 241N into the cavity 241RC results in the generation of ultrasonic energy in the manner of a Hartmann-type whistle device. Gas flowing through the whistle device 241 flows out from the device through an aperture 241A in the whistle body 241C, contributing to gas lift in the column 225.

In the embodiment shown, the whistle devices 241 may be tuned to generate ultrasonic energy having a frequency in the range from 20 to around 26 kHz. Higher frequencies may be useful in some embodiments as noted above. It is to be understood that the skilled person will be capable of determining an optimum gas pressure for driving the whistle devices, and an optimum distance between the nozzle member 241N and receptor member 241R, to generate ultrasonic energy of appropriate frequency and amplitude. The present applicant has determined that with the whistle devices 241 at a depth of 2 m or more below the surface of fresh water and a process gas pressure of 1-4 bar, optionally in the range 1-5 bar, ultrasonic energy of suitable amplitude and frequency may be generated by suitable adjustment of the distance between the nozzle member 241N and cavity 241RC. A distance between the receptor member 141R and nozzle 141N may be adjusted by means of the screw thread by rotation of the receptor member 141R. In some embodiments, the drive gas for driving the whistle devices 241 is supplied at a pressure of around 1.5 bar to whistle devices 241 at a depth of 2 m below a level of liquid in the liquid storage tank 110. Higher pressures than 5 bar may be useful in some embodiments.

Embodiments of the present invention have been found to enable the highly efficient generation of microbubbles in liquid in the column of the converter portion 115, 215. When the microbubbles are subject to ultrasonic energy by the ultrasonic energy generator, cavitation of the microbubbles takes place. It is believed that, if the microbubbles contain carbon dioxide, cavitation in collapsing microbubbles results in the conversion of carbon dioxide to hydrocarbon gas and oxygen as described above.

In some embodiments, methane gas may be generated. In some embodiments, one or more other hydrocarbon compounds may be generated in addition or instead. For example, methanol and/or ethanol may be produced in some embodiments, in addition to or instead of methane. Other alkanes may be produced in some embodiments such as ethane, propane and one or more other alkanes in addition or instead. One or more catalyst materials may be provided in the liquid in the liquid holding tank 110, 210, in order to promote the formation of particular products.

Non-hydrocarbon gases may be produced exclusively in some embodiments.

Figure 9:
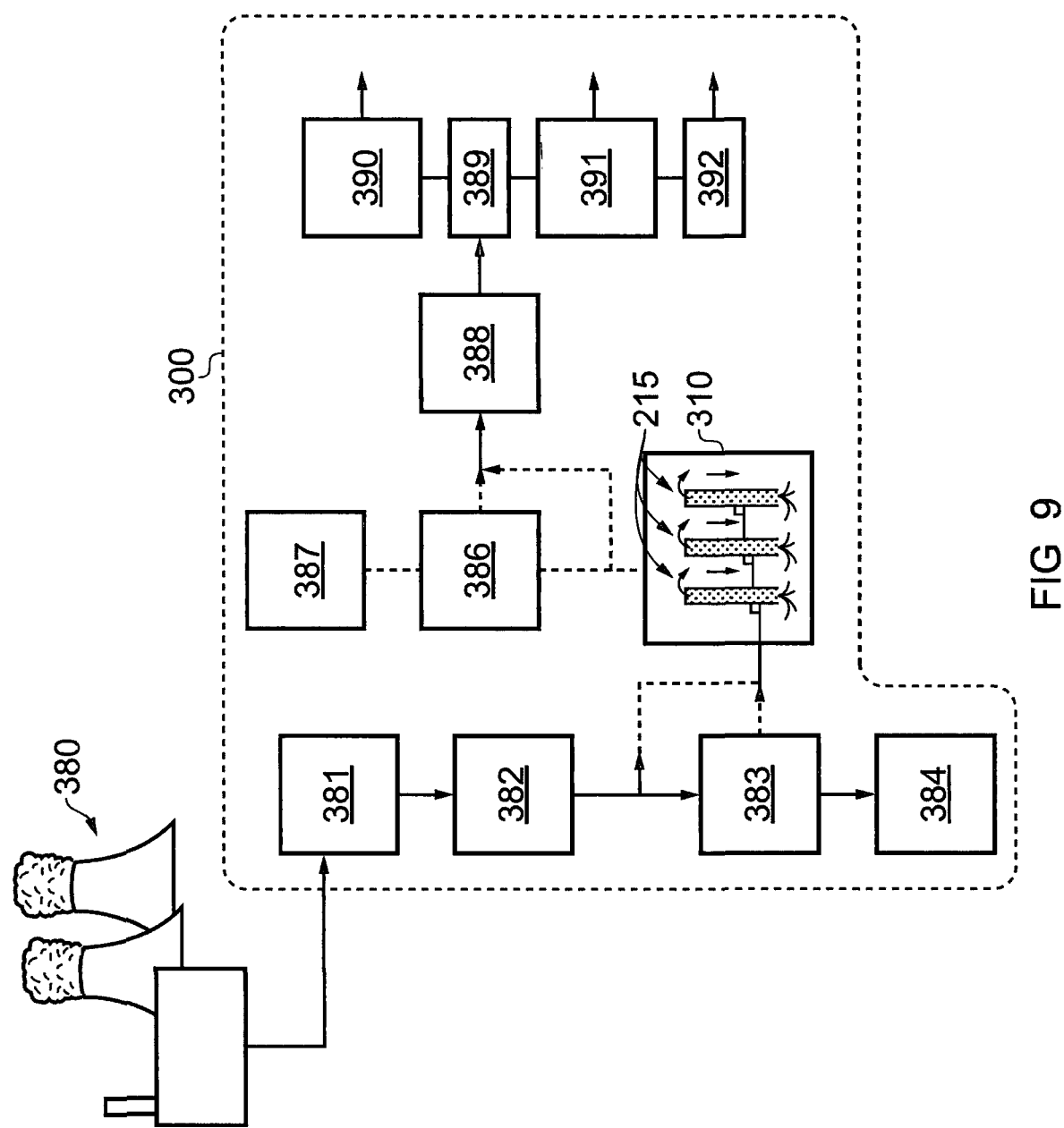
FIG. 9 is a schematic illustration of a boiler exhaust gas processing system according to an embodiment of the present invention arranged to process power station boiler exhaust gases.

FIG. 9 is a schematic illustration showing a coal, oil or gas-fired power generating station 380 connected to a boiler exhaust gas conversion apparatus 300 that is configured to convert a process gas comprising carbon dioxide into methane gas and oxygen gas. The apparatus 300 has a liquid holding tank 310 in which are provided three converter portions 215 substantially as described and illustrated with respect to FIG. 5(a) to FIG. 8. Other numbers of converter portions 215 may also be useful, such as 1, 2, 4, 5, 10 or any other suitable number.

The apparatus 300 is arranged to receive process gas in the form of power station boiler exhaust gas and to pass the gas initially through a gas cooling scrubber 381. The scrubber 381 cools the gas by means of a water cooling system, and in addition removes particulates suspended in the gases such as soot particles. One or more other constituents of the gas may be removed in addition or instead in some embodiments, such as $SO_x$ and/or $NO_x$.

The process gas then passes through a gas compression system 382 before being passed either directly to the converter portions 215 or to the converter portions 215 via a nitrogen separation system 383. The separation system 383 is arranged to separate nitrogen gas from the process gas. The separation system 383 may comprise a membrane separation system, optionally a hollow fibre membrane separation (HFMS) system, configured to remove nitrogen. The separated nitrogen is passed to a nitrogen gas output handling system 384 by means of which nitrogen may be exhausted to atmosphere, stored, or used for one or more other purposes. Remaining gas is fed to the converter portions 215.

As described above, the holding tank has three converter portions 215 each arranged to generate microbubbles of process gas in a column 225 thereof that is immersed in liquid in the holding tank 310. The converter portions 215 are arranged to subject the microbubbles to high intensity ultrasonic radiation. Gas that has passed through the column 225 of at least one of the converter portions 215 is drawn from the liquid tank 310 and fed to a gas compression system 388. The apparatus 300 is arranged to allow the gas to be fed directly to the gas compression system 388 or to be fed to the gas compression system 388 via a nitrogen separation system 386. If the apparatus 300 is operated such that gas is fed to the gas compression system 388 via the nitrogen separation system 386, nitrogen separated from the gas by the nitrogen separation system 386 is fed to a nitrogen gas output handling system 387 where nitrogen may be exhausted to atmosphere, stored, or used for one or more other purposes.

In some use scenarios, the boiler exhaust gas conversion apparatus 300 is arranged such that gas flowing through the system to gas compression system 388 passes through only one of the two nitrogen gas separation systems 383, 386. In some alternative scenarios, the apparatus 300 is arranged to allow gas to flow through both of the separation systems 383, 386.

In some embodiments the apparatus 300 has only one of the two nitrogen gas separation systems 383, 386. In some embodiments the apparatus 300 may not be configured to pass the gas through any separate nitrogen separator 383, 386.

Gas passing through gas compression system 388 is subsequently fed to a methane separator 389 that separates methane from gas entering the separator 389. The separated methane is stored in a methane storage tank 390.

Gas from which methane has been separated is fed from the separator 389 to an oxygen separator 391 that separates oxygen from the gas fed to the separator 391. Separated oxygen is stored in an oxygen storage tank 392. Gas from which oxygen has been separated by the separator 391 may be subject to further treatment before being exhausted.

Thus, the apparatus 300 may be employed to generate and separate hydrocarbons and oxygen from power station boiler exhaust gas, in particular from carbon dioxide contained in power station boiler exhaust gas.

It is to be understood that the nitrogen separation systems 383, 386 may each have a compressor for compressing gas before it passes through a separator portion thereof, such as a membrane separator.

Separation of gases in embodiments of the present invention may be performed by any suitable separator such as a membrane separator, for example a hollow fibre membrane separator HFMS, or any other suitable separator.

In some embodiments, apparatus is provided for converting carbon dioxide to hydrocarbon fuel, the apparatus being powered by electrical energy. The primary consumers of the electrical energy are gas compressors, gas separator devices and control modules arranged to control the apparatus. The apparatus is employed to convert carbon dioxide to hydrocarbon gas, liquid or solid using electrical energy from renewable sources such as solar energy, geothermal energy, wind energy, wave or tidal energy. In the present embodiment the apparatus is arranged to convert carbon dioxide to methane. In some embodiments, the apparatus may be suitable for installation in a domestic or commercial building environment and the methane gas used to heat water or other substance when required, for example for washing or cooking. In some embodiments carbon dioxide so generated may be recovered back to the apparatus for conversion back to methane. Other arrangements may also be useful.

In some embodiments the apparatus may be provided in combination with a renewal energy capture device or apparatus such as a solar photovoltaic energy generator having a solar panel, power inverter and control electronics.

Figure 10:
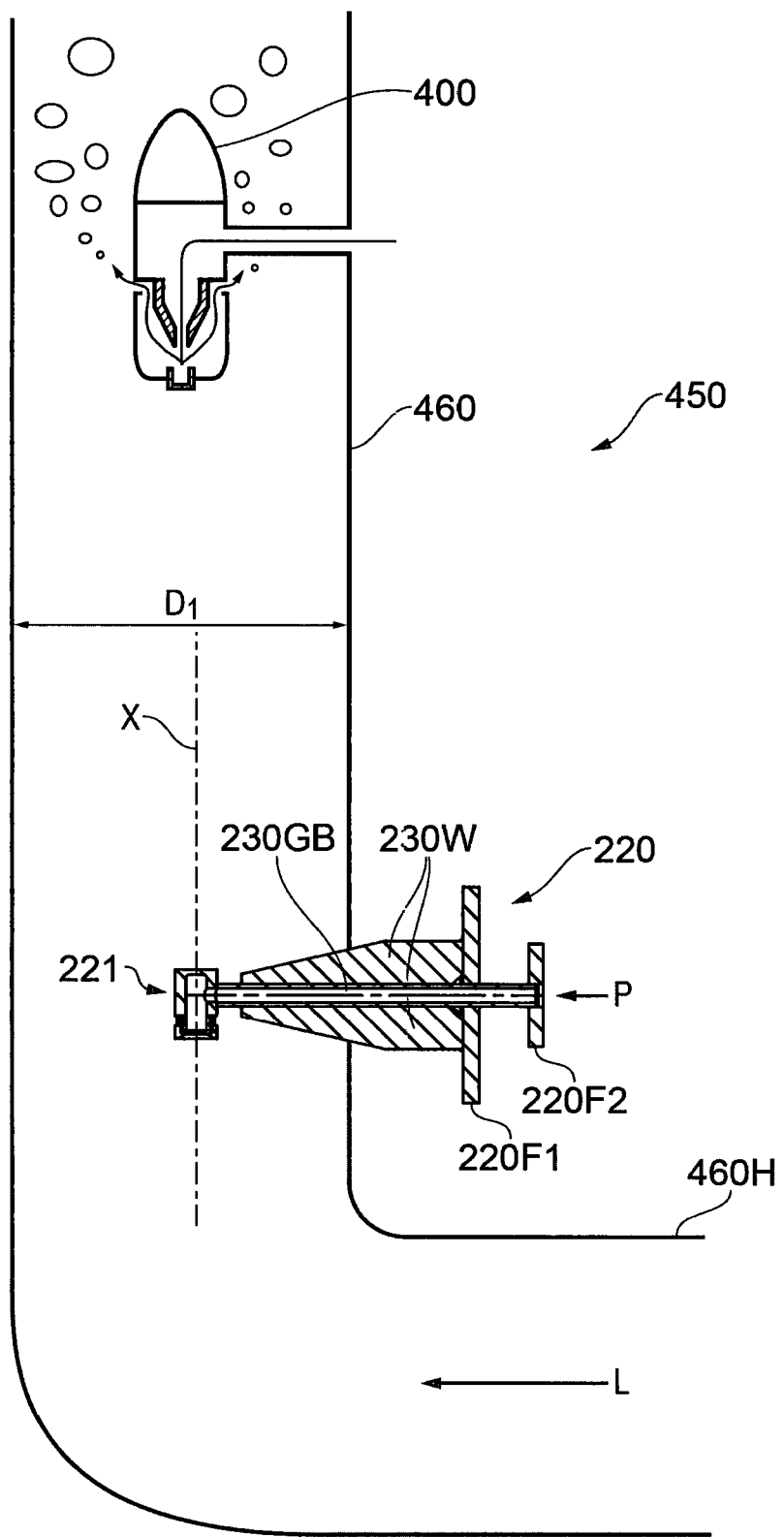
FIG. 10 is a schematic illustration of a further embodiment of a gas lift pump apparatus in which is provided a microbubble generator of the embodiment of FIG. 6.

FIG. 10 is a schematic illustration showing the use of the novel microbubble generator 220 of the embodiment shown in FIGS. 5 and 6 in an example of a gas lift pump apparatus 450, such as that for circulating liquid in a liquid storage or ballast tank of a vessel, e.g. a ship or other water-going vessel, such as for the purpose of killing aquatic nuisance species (ANS) therein. It is to be understood that the microbubble generator 220, or other embodiments of same within the scope of this aspect of the invention defined herein, may be utilised in other embodiments and constructions of gas lift apparatus, including those disclosed in WO2013/093527 (the entire contents of which are incorporated herein by reference).

As shown in FIG. 10, the gas lift pump apparatus 450 includes the novel microbubble generator 220 as shown in FIG. 5 and shown in enlarged detail in FIG. 6, as well as sonic energy generator 400, provided in a generally vertical (in use) gas lift column 460. The sonic energy generator 400 may be any example sonic energy generator as used in other embodiments of the present invention in others of its aspects, or indeed may be a combined fluid delivery device/sonic energy generator as disclosed and illustrated in any embodiment of WO2013/093527. The column 460 is filled with a liquid, e.g. water (such as that in a ballast tank of a vessel in which the apparatus may be provided), which is pumped therethrough as a flow L thereof under the effect of gas lift.

The microbubble generator 220 is operable to inject a flow of gas P, such as carbon dioxide, into the column 460 via the bubbler 221, which output gas flow rises towards the sonic energy generator 400. Preferably the bubbler 221 is situated substantially coaxially within the column 460 (i.e. aligned along common longitudinal axis X), in order to enhance the homogeneity of the flow of gas microbubbles (with respect to the cross-sectional area $D_1$ of the column 460) as it exits the bubbler 221 and rises in the column 460 towards the sonic energy generator 400. The apparatus 450 is operable to pump the water or other liquid L through the column 460 from a draw tube 460H by the effect of gas lift due to the gas injected into the column via the sonic energy generator 400 as well as bubbler 221. As noted above, in some embodiments drive gas used to cause the sonic energy generator 400 to generate sonic energy may be recirculated by the apparatus 450 rather than being exhausted into the gas lift column 460.

Gas bubbles are formed within, and ejected from, the bubbler 221 of the bubble generator 220 in the same manner as described above in relation to FIG. 6. A size of the bubbles is reduced to micron-order levels by the shear forces experienced as the gas P is injected via the conduit 230GB through the bubbler 221 and out the bottom (outlet) thereof.

As disclosed in WO2013/093527, this example arrangement of gas lift pump apparatus shown in FIG. 10, utilising the novel microbubble generator 220 (or its various other novel embodiments defined herein), is useful for the treatment of e.g. ballast water in waterborne vessels, e.g. for killing bacterial ANS as well as non-bacterial ANS.

Although the embodiment of FIG. 10 shows the microbubble generator 220 positioned in the flowstream of liquid L from the draw tube 460H, it is to be understood that various alternative configurations of these components may be employed, as taught and disclosed for example in WO2013/093527. For instance the microbubble generator 220 may alternatively be provided at a base of a column having a closed lower end, with there being provided a dedicated separate inlet for supply of water or other liquid thereinto to be pumped by the apparatus, for example in a similar manner to the liquid inlet 120C of the apparatus of FIG. 1.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Gas conversion apparatus for converting carbon dioxide in a process gas to a plurality of hydrocarbon gases, the apparatus comprising:
    a compressor configured to supply the process gas into a liquid water medium;
    a whistle device configured to generate ultrasonic energy, wherein the apparatus is configured to launch the ultrasonic energy generated by the whistle device directly into the liquid water medium such that the process gas in the liquid water medium is directly exposed to the ultrasonic energy so that the carbon dioxide in the process gas is converted to the plurality of hydrocarbon gases; and
    a gas separator configured to collect and separate the plurality of hydrocarbon gases from the liquid water medium, and to return some of the plurality of hydrocarbon gases to the liquid water medium for further exposure to the ultrasonic energy.

2. The apparatus of claim 1, wherein the whistle device is configured to generate the ultrasonic energy when drive gas is driven through the whistle device.

3. The apparatus of claim 2, further configured to feed the drive gas into the liquid water medium after driving the drive gas through the whistle device.

4. The apparatus of claim 2, wherein the process gas provides the drive gas.

5. The apparatus of claim 1, further comprising:
a gas lift column through which the liquid water medium is pumped by gas lift; and
wherein the compressor is configured to supply the process gas into the column, wherein the apparatus is configured to launch the ultrasonic energy generated by the whistle device into the liquid water medium in the column such that the process gas passing through the column by gas lift is exposed to the ultrasonic energy generated by the whistle device.

6. The apparatus of claim 5, further configured to feed drive gas into the liquid water medium in the gas lift column such that the drive gas is exposed to ultrasonic energy in the column.

7. The apparatus of claim 5, further comprising a microbubble generator that is configured to cause microbubbles of the process gas to be generated in the liquid water medium and to be subject to irradiation by the ultrasonic energy generated by the whistle device, and wherein the microbubble generator is configured to introduce microbubbles of the process gas into the liquid water medium in the column upstream of the whistle device.

8. The apparatus of claim 1, wherein the process gas consists essentially of carbon dioxide.

9. The apparatus of claim 1, wherein the apparatus is installed in a liquid water storage tank.

10. The apparatus of claim 9, wherein the liquid water storage tank contains liquid water, and wherein the liquid water is provided with particles of a catalyst material dispersed or suspended therein.

11. The apparatus of claim 10, wherein the catalyst particles comprise at least one selected from amongst iron and a hematite-bearing compound, or wherein the catalyst particles consist substantially of hematite.

12. The apparatus of claim 1, wherein the apparatus is coupled to a power generating station, and wherein combustion gases generated by the power generating station provide at least a portion of the process gas of the apparatus.

13. A fuel burning engine in combination with the apparatus of claim 1, wherein combustion gases generated by the engine provide at least a portion of the process gas of the apparatus.

14. The apparatus of claim 1, wherein the gas separator is a membrane separator.

15. The apparatus of claim 14, wherein the membrane separator is a hollow fibre membrane separator.

16. A method of converting carbon dioxide in a process gas to a plurality of hydrocarbon gases, the method comprising:
introducing the process gas into a liquid water medium;
generating ultrasonic energy via a whistle device, comprising launching ultrasonic energy generated by the whistle device into the liquid water medium such that the process gas is exposed to the ultrasonic energy so as to convert the carbon dioxide to the plurality of hydrocarbon gases;
collecting and separating the plurality of hydrocarbon gases via a gas separator; and
returning some of the collected and separated hydrocarbon gases to the liquid water medium for further exposure to the ultrasonic energy.

17. The method of claim 16, wherein generating the ultrasonic energy via the whistle device comprises driving a drive gas through the whistle device, and further comprising feeding the drive gas into the liquid water medium after passing the drive gas through the whistle device, wherein the process gas provides the drive gas.

18. The method of claim 16, further comprising causing microbubbles to be generated in the liquid water medium and subjected to irradiation by the ultrasonic energy generated by the whistle device.

19. The method of claim 16, wherein introducing the process gas into the liquid water medium comprises introducing the process gas into a column of a gas lift pump apparatus and causing pumping of the liquid water medium through the column by gas lift, and whereby launching the ultrasonic energy generated by the whistle device into the liquid water medium comprises launching the ultrasonic energy into the liquid water medium in the column whereby the process gas passing through the column is exposed to ultrasonic energy.

20. The method of claim 16, wherein the process gas is exhaust gas from a power station boiler, and wherein introducing the process gas into the liquid water medium comprises receiving the process gas from the power station boiler.

* * * * *